US012662446B2

(12) United States Patent
Mahapatra et al.

(10) Patent No.: US 12,662,446 B2
(45) Date of Patent: Jun. 23, 2026

(54) PROCESS FOR THE SYNTHESIS OF ANTHRANILIC ACID/AMIDE COMPOUNDS AND INTERMEDIATES THEREOF

(71) Applicant: PI INDUSTRIES LIMITED, Udaipur-Rajasthan (IN)

(72) Inventors: Tridib Mahapatra, Udaipur-Rajasthan (IN); Pranab Kumar Patra, Udaipur-Rajasthan (IN); Alexander G.M. Klausener, Pulheim (DE); Sanjib Mal, Udaipur-Rajasthan (IN); Raju Sharma, Hoshiarpur-Punjab (IN)

(73) Assignee: PI INDUSTRIES LTD., Udaipur-Rajasthan (IN)

( * ) Notice: Subject to any disclaimer, the term of this patent is extended or adjusted under 35 U.S.C. 154(b) by 553 days.

(21) Appl. No.: 18/026,610

(22) PCT Filed: Sep. 16, 2021

(86) PCT No.: PCT/IB2021/058438

§ 371 (c)(1),
(2) Date: Mar. 16, 2023

(87) PCT Pub. No.: WO2022/058916

PCT Pub. Date: Mar. 24, 2022

(65) Prior Publication Data

US 2023/0339844 A1 Oct. 26, 2023

(30) Foreign Application Priority Data

Sep. 17, 2020 (IN) ............................. 202011040285

(51) Int. Cl.

| | |
|---|---|
| ***C07C 221/00*** | (2006.01) |
| ***C07C 227/18*** | (2006.01) |
| ***C07C 231/02*** | (2006.01) |
| ***C07C 253/14*** | (2006.01) |

(52) U.S. Cl.

CPC .......... *C07C 221/00* (2013.01); *C07C 227/18* (2013.01); *C07C 231/02* (2013.01); *C07C 253/14* (2013.01)

(58) Field of Classification Search

CPC ... C07C 221/00; C07C 227/18; C07C 231/02; C07C 253/14; C07C 227/02; C07C 231/10; C07C 253/30; C07C 225/22; C07C 229/56; C07C 237/30; C07C 255/58; Y02P 20/55; C07D 265/26; C07D 401/04

See application file for complete search history.

(56) References Cited

U.S. PATENT DOCUMENTS

| | | | |
|---|---|---|---|
| 2009/0306372 A1 | 12/2009 | Davis et al. | |
| 2014/0194623 A1 | 7/2014 | Pazenok et al. | |
| 2020/0062722 A1 | 2/2020 | Watts et al. | |

FOREIGN PATENT DOCUMENTS

| | | | |
|---|---|---|---|
| WO | WO-2008010897 A2 * | 1/2008 | ........... C07D 231/16 |
| WO | WO-2013030100 A1 * | 3/2013 | ........... C07D 401/14 |
| WO | 2018154414 A1 | 8/2018 | |
| WO | 2020170092 A1 | 8/2020 | |
| WO | WO-2020170178 A1 * | 8/2020 | ........... C07D 401/04 |
| WO | 2020170092 A9 | 11/2021 | |

OTHER PUBLICATIONS

Sreenivasa S. et al: "2-Amino-5-fluorobenzoic acid", Acta Crystallographica Section E Structure Reports Online, vol. 69, No. 3, pp. 0387-0387. (Year: 2013).*

Leroux Frederic et al, "The "Off-Shore" Construction of Optionally Substituted 4-Trifluoromethyl-2-quinolinones", European Journal of Organic Chemistry,vol. 2006, No. 14, Jul. 1, 2006 (Jul. 1, 2006), p. 3147-3151, XP055878850 DOI: 10.1002/ejoc.200600140 external link ISSN:1434-193X.

Perkin J C S et al, "The Chemistry of Nitrilium Salts. Phenol Ethers with Nitriles and Trifluoromethanesulphonic Acid Part 1. Acylation of Phenols and", J. Chem. Soc., Perkin Trans 1,vol. 12, Jan. 1, 1980 (Jan. 1, 1980), p. 2894-2900, XP055861751 DOI: 10.1039/P19800002894.

Sreenivasa S. et al, "2-Amino-5-fluorobenzoic acid", Mar. 15, 2013 (Mar. 15, 2013), vol. 69, No. 3, p. o387-o387, Retrieved from the Internet: URL:https://journals.iucr.org/e/issues/2013/03/00/hb7040/hb7040.pdf XP055879695 DOI: 10.1107/S160053681300408X.

PCT ISR Jan. 31, 2022 (5 Pages).

PCT WR-OPN (8 Pages).

* cited by examiner

*Primary Examiner* — Deborah D Carr

(74) *Attorney, Agent, or Firm* — Lippes Mathias LLP

(57) ABSTRACT

The present invention disclosed a process for the synthesis of compound of formula (Z) or a salt thereof,

Z

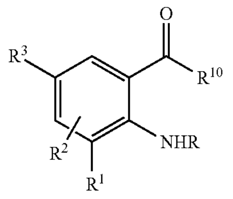

wherein, R, $R^1$, $R^2$, $R^3$ and $R^{10}$ are as defined in the detailed description. The process further comprises the synthesis of an anthranilic diamide compound of formula (I).

17 Claims, No Drawings

PROCESS FOR THE SYNTHESIS OF ANTHRANILIC ACID/AMIDE COMPOUNDS AND INTERMEDIATES THEREOF

This application is a National Stage Entry of International Application No. PCT/IB2021/058438, filed Sep. 16, 2021, which claims priority to Indian Application No. 202011040285, filed Sep. 17, 2020 in India, the contents of which are incorporated by reference herein.

FIELD OF THE INVENTION

The present invention relates to a process for the synthesis of a compound of formula (Z) or a salt thereof. Further the present invention relates to a process for the synthesis of anthranilic diamides of formula (I) from substituted anilines of formula (II), making use of compounds of formula (Z).

BACKGROUND OF THE INVENTION

Anthranilic diamides are a commercially important class of synthetic insecticides that bind to the ryanodine receptor with selective potency against insects versus mammalian forms of this receptor. The first commercialized anthranilic diamide of this class, chlorantraniliprole, has an exceptional activity against lepidopteran pests. The second anthranilic diamide product of the same class, cyantraniliprole, has an excellent cross-spectrum activity against a range of insect orders, including both lepidopteran and hemipteran pests. WO2003015518, WO2003015519, WO2004067528, WO2005077934, and WO20100069502 have disclosed the use of anthranilic diamides for controlling invertebrate pests such as arthropods.

These anthranilic diamide compounds can be prepared from 3,5-substituted 2-amino-N-alkylbenzamide compounds as intermediates. WO2012103436 discloses a process for the preparation of 2-amino-benzamide compounds from 2-halo-anilines. The synthesis of certain 3,5-substituted 2-amino-N-alkylbenzamide compounds and their utility as intermediates for the preparation of corresponding insecticidal anthranilic diamide compounds has been disclosed in WO2004067528, WO2006062978 and WO2006068669. Further, the process for the synthesis of an anthranilic diamide compounds or 3,5-substituted 2-amino-N-alkyl-benzamide compounds or intermediates thereof has been disclosed in WO2012103436 and WO2013117601.

WO2012103436 and WO2013117601 described the preparation of anthranilic amides from 2-halo aniline derivatives using hazardous carbon monoxide gas and an appropriate palladium catalyst, which as such is a disadvantage. Another drawback is that the starting materials, tetra-substituted aniline compounds, are costly.

The process described in *Journal of Heterocyclic Chemistry,* 53(4), 1036-1045; 2016 involves five steps in order to achieve the synthesis of an anthranilic amide compound. Furthermore, the process described in WO2012161313 involves the use of the n-butyl lithium, which is difficult to handle at large scale.

The processes described in the above mentioned literature are laborious as well as having disadvantages that are mentioned herein above. There is a need to find a simple, efficient, and industrially economical process for the preparation of anthranilic (di)amide compounds. Accordingly, the present invention provides a simple, environment-friendly and cost-efficient process for the preparation of anthranilic diamides and intermediates thereof, based on easily available starting materials.

OBJECTIVE OF THE INVENTION

The main objective of the present invention is to provide a process for the synthesis of substituted anthranilic acid/amide compounds of formula (Z) or of salts thereof.

Another objective of the present invention is to provide a process for the synthesis of trihalo substituted phenylethanones of formula (Z).

Yet another objective of the present invention is to provide a simple, environment-friendly and cost-effective process for the synthesis of anthranilic diamides of formula (I), based on readily available starting materials.

SUMMARY OF THE INVENTION

Accordingly, the present invention provides a process for the synthesis of compounds of formula (Z) from substituted anilines of formula (II).

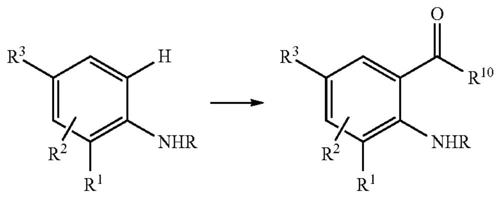

II Z wherein,

R is selected from the group comprising of hydrogen or $COR^{11}$;

wherein, $R^{11}$ is selected from the group comprising of $C_1$-$C_4$ alkoxy, O-benzyl or O-phenyl;

$R^1$ and $R^2$ are independently selected from the group comprising of hydrogen, halogen, $C_1$-$C_4$ alkyl, $C_1$-$C_4$ haloalkyl or $C_3$-$C_6$ cycloalkyl;

$R^3$ is selected from the group comprising of hydrogen, halogen, cyano, $C_1$-$C_4$ haloalkyl or $C_3$-$C_6$ cycloalkyl;

$R^{10}$ is selected from the group comprising of $CX_3$, $OR^9$, or $NR^{4a}R^{4b}$ X represents halogen;

$R^9$ is selected from the group comprising of hydrogen or $C_1$-$C_4$ alkyl;

$R^{4a}$ and $R^{4b}$ are independently selected from the group comprising of hydrogen, $C_1$-$C_4$ alkyl, $C_3$-$C_6$ cycloalkyl, $C_3$-$C_6$ cycloalkyl-$C_1$-$C_4$ alkyl; or $NR^{4a}R^{4b}$ is representing $—N{=}S(R^7R^8){=}(O)_n$;

n represents an integer from 0-1;

$R^7$ and $R^8$ are independently selected from the group comprising of $C_1$-$C_4$ alkyl, $C_1$-$C_4$ haloalkyl, $C_3$-$C_6$ cycloalkyl or $C_3$-$C_6$ cycloalkyl-$C_1$-$C_4$ alkyl.

The present invention further provides a process for the synthesis of anthranilic diamides of formula (I), Formula (I)

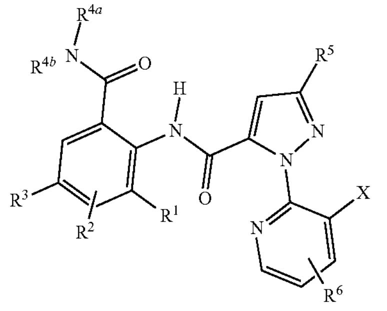

wherein, $R^1$ and $R^2$ are independently selected from the group comprising of hydrogen, halogen, $C_1$-$C_4$ alkyl, $C_1$-$C_4$ haloalkyl or $C_3$-$C_6$ cycloalkyl;

$R^3$ is selected from the group comprising of hydrogen, halogen, cyano, $C_1$-$C_4$ haloalkyl or $C_3$-$C_6$ cycloalkyl;

$R^{4a}$ and $R^{4b}$ are independently selected from the group comprising of hydrogen, $C_1$-$C_4$ alkyl, $C_3$-$C_6$ cycloalkyl, $C_3$-$C_6$ cycloalkyl-$C_1$-$C_4$ alkyl; or $NR^{4a}R^{4b}$ represents $—N{=}S(R^7R^8){=}(O)_n$; wherein $R^7$ and $R^8$ are independently selected from the group comprising of $C_1$-$C_4$ alkyl, $C_1$-$C_4$ haloalkyl $C_3$-$C_6$ cycloalkyl or $C_3$-$C_6$ cycloalkyl $C_1$-$C_4$ alkyl;

n represents an integer from 0-1;

$R^5$ is selected from the group comprising of halogen, $C_1$-$C_4$ alkyl, $C_1$-$C_4$ haloalkyl, $CHF_2$, $CF_3$, $C_1$-$C_4$ alkoxy; $OCF_2H$, $OCH_2CF_3$, or -A-$C_3$-$C_5$ heterocyclyl;

wherein -A- is selected from the group comprising of direct bond, $CHR^6$, —O— or —S—; and said heterocyclyl may optionally be substituted with one or more group selected from hydrogen, halogen, cyano, $C_1$-$C_4$ alkyl or $C_1$-$C_4$ haloalkyl;

$R^6$ is selected from the group comprising of hydrogen, halogen, cyano, $C_1$-$C_4$ alkyl or $C_1$-$C_4$ haloalkyl;

X is halogen;

from a substituted anilines of formula (II);

II

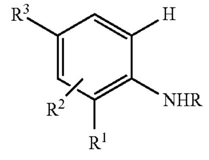

wherein, $R^1$ and $R^2$ are independently selected from the group comprising of hydrogen, halogen, $C_1$-$C_4$ alkyl, $C_1$-$C_4$ haloalkyl or $C_3$-$C_6$ cycloalkyl;

$R^3$ is selected from the group comprising of hydrogen, halogen, cyano, $C_1$-$C_4$ haloalkyl or $C_3$-$C_6$ cycloalkyl;

R is selected from the group comprising of hydrogen or $COR^{11}$;

wherein, $R^{11}$ is selected from the group comprising of $C_1$-$C_4$ alkoxy, O-benzyl or O-phenyl; according to the reaction scheme as depicted below,

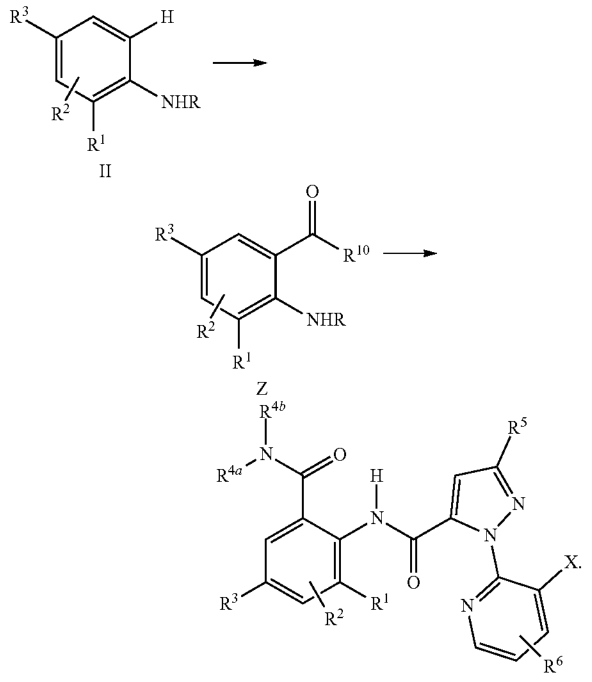

II

Z

I

In one aspect, the present invention provides a process for the synthesis of a trihalo substituted phenylethanone of formula (Z), wherein $R^{10}$ is $CX_3$ from a substituted aniline of formula (II).

In another aspect, the present invention provides a process for the synthesis of an anthranilic acid of formula (Z), wherein $R^{10}$ is $OR^9$ and $R^9$ is hydrogen; or an anthranilic ester of formula (Z), wherein $R^{10}$ is $OR^9$ and $R^9$ is $C_1$-$C_4$ alkyl from substituted aniline of formula (II).

In yet another aspect, the present invention provides a process for the synthesis of a substituted anthranilic amide of formula (Z), wherein $R^{10}$ is $NR^{4a}$ $R^{4b}$ from substituted aniline of formula (II).

DETAILED DESCRIPTION OF THE INVENTION

The definitions provided herein for the terminologies used in the present disclosure are for illustrative purpose only and in no manner limit the scope of the present invention disclosed in the present disclosure.

As used herein, the terms "comprises", "comprising", "includes", "including", "has", "having", "contains", "containing", "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

Further, unless expressly stated to the contrary, "or" refers to an inclusive "or" and not to an exclusive "or". For example, a condition A "or" B is satisfied by any one of the following: A is true (or present) and B is false (or not present), A is false (or not present) and B is true (or present), and both A and B is true (or present).

Also, the indefinite articles "a" and "an" preceding an element or component of the present invention are intended to be non-restrictive regarding the number of instances (i.e. occurrences) of the element or component. Therefore "a" or "an" should be read to include one or at least one, and the singular word form of the element or component also includes the plural unless the number is obviously meant to be singular.

The meaning of various terms used in the description shall now be illustrated.

The term "alkyl", used either alone or in compound words such as "haloalkyl" or —N(alkyl)—includes straight-chain or branched $C_1$ to $C_{12}$ alkyl, more preferably $C_1$ to $C_6$ alkyl, most preferably $C_1$ to $C_4$ alkyl. Representative examples of alkyl include methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl or the different isomers. If the alkyl is at the end of a composite substituent, as, for example, in alkylcycloalkyl, the part of the composite substituent at the start, for example the cycloalkyl, may be mono- or poly-substituted identically or differently and independently by alkyl. The same also applies to composite substituents in which other radicals, for example alkenyl, alkynyl, hydroxyl, halogen, carbonyl, carbonyloxy and the like, are at the end.

The term "cycloalkyl" means alkyl closed to form a ring. Representative examples include but are not limited to cyclopropyl, cyclobutyl, cyclopentyl and cyclohexyl. This definition also applies to cycloalkyl as a part of a composite substituent, for example cycloalkylalkyl etc., unless specifically defined elsewhere.

The term "cycloalkylalkyl" means cycloalkyl substituent on alkyl, for example, cyclopropyl or cyclobutyl or cyclopentyl are substituted on any carbon of $C_1$-$C_6$ alkyl. Representative examples of cycloalkylalkyl include cyclopropyl methyl, cyclopropyl ethyl.

The term "alkoxy" used either alone or in compound words included $C_1$ to $C_{10}$ alkoxy, most preferably $C_1$ to $C_6$ alkoxy. Examples of alkoxy include methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy and the different isomers. This definition also applies to alkoxy as a part of a composite substituent, for example haloalkoxy, alkynylalkoxy, etc., unless specifically defined elsewhere.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Non-limiting examples of "haloalkyl" include chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 1,1-dichloro-2,2,2-trifluoroethyl, and 1,1,1-trifluoroprop-2-yl. This definition also applies to haloalkyl as a part of a composite substituent, for example haloalkylaminoalkyl etc., unless specifically defined elsewhere.

The term "hetero" in connection with rings refers to a ring in which at least one ring atom is not carbon and which can contain 1 to 4 heteroatoms independently selected from the group consisting of nitrogen, oxygen and sulfur, provided that each ring contains no more than 4 nitrogen, no more than 2 oxygen and no more than 2 sulfur.

The term "aromatic" indicates that the Huckel rule is satisfied and the term "non-aromatic" indicates that the Huckel rule is not satisfied.

The term "heterocycle" or "heterocyclic" or "heterocyclyl" includes "aromatic heterocycle" or "heteroaryl bicyclic ring system" and "nonaromatic heterocycle" or polycyclic or bicyclic (spiro, fused, bridged, non-fused) ring compounds in which ring may be aromatic or non-aromatic, wherein the heterocycle ring contains at least one heteroatom selected from N, O, $S(O)_{0-2}$, and/or C ring member of the heterocycle may be replaced by C(═O) and C(═S).

The term "non-aromatic heterocycle" or "non-aromatic heterocyclic" means three- to ten-membered, preferably three- to six-membered, saturated or partially unsaturated heterocycle containing one to four heteroatoms, selected from the group of oxygen, nitrogen and sulphur; mono, bi- or tricyclic heterocycles which contain, in addition to carbon ring members, one to three nitrogen atoms and/or one oxygen or sulphur atom or one or two oxygen and/or sulphur atoms; if the ring contains more than one oxygen atom, they are not directly adjacent; for example (but not limited to) oxiranyl, aziridinyl, oxetanyl, azetidinyl, thietanyl, tetrahydrofuranyl, tetrahydrothienyl, pyrrolidinyl, isoxazolidinyl, isothiazolidinyl, pyrazolidinyl, oxazolidinyl, thiazolidinyl, imidazolidinyl, oxadiazolidinyl, thiadiazolidinyl, triazolidinyl, dihydrofuryl, dihydrothienyl, pyrrolinyl, isoxazolinyl, isothiazolinyl, dihydropyrazolyl, dihydrooxazolyl, dihydrothiazolyl, piperidinyl, pyrazynyl, morpholinyl, thiomorphlinyl, 1,3-dioxany, tetrahydropyranyl, tetrahydrothienyl; wherein these rings are attached to the skeleton via one of the carbon or nitrogen of said rings. This definition also applies to heterocyclyl as a part of a composite substituent, for example heterocyclylalkyl etc., unless specifically defined elsewhere.

The term "heteroaryl" or "aromatic heterocyclic" means 5-membered, fully unsaturated monocyclic ring system containing one to four heteroatoms selected from the group of oxygen, nitrogen and sulphur; if the ring contains more than one oxygen atom, they are not directly adjacent; 5-membered heteroaryl containing one to four nitrogen atoms or one to three nitrogen atoms and one sulphur or oxygen atom; 5-membered heteroaryl groups which, in addition to carbon atoms, may contain one to four nitrogen atoms or one to three nitrogen atoms and one sulphur or oxygen atom as ring members, for example (but not limited thereto) furyl, thienyl, pyrrolyl, isoxazolyl, isothiazolyl, pyrazolyl, oxazolyl, thiazolyl, imidazolyl, oxadiazolyl, thiadiazolyl, triazolyl, tetrazolyl; wherein these rings are attached to the skeleton via one of the carbon or nitrogen of said rings, To achieve at least one of the above defined objectives, the present invention provides a process for the synthesis of compound of formula (Z).

In another aspect, the present invention provides a process for the synthesis of a compound of formula (Z) or a salt thereof,

Z

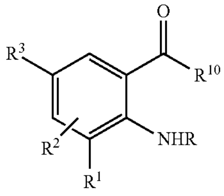

wherein, $R^1$ and $R^2$ are independently selected from the group comprising of hydrogen, halogen, $C_1$-$C_4$ alkyl, $C_1$-$C_4$ haloalkyl or $C_3$-$C_6$ cycloalkyl;

$R^3$ is selected from the group comprising of hydrogen, halogen, cyano, $C_1$-$C_4$ haloalkyl or $C_3$-$C_6$ cycloalkyl;

R is selected from the group comprising of hydrogen or $COR^{11}$;

wherein, $R^{11}$ is selected from the group comprising of $C_1$-$C_4$ alkoxy, O-benzyl or O-phenyl;

$R^{10}$ is selected from the group comprising of $CX_3$, $OR^9$, or $NR^{4a}R^{4b}$ X represents halogen;

$R^9$ is selected from the group comprising of hydrogen or $C_1$-$C_4$ alkyl;

$R^{4a}$ and $R^{4b}$ are independently selected from the group comprising of hydrogen, $C_1$-$C_4$ alkyl, $C_3$-$C_6$ cycloalkyl, $C_3$-$C_6$ cycloalkyl-$C_1$-$C_4$ alkyl; or $NR^{4a}R^{4b}$ represent —N═S($R^7R^8$)═$(O)_n$;

n represents an integer from 0-1;

$R^7$ and $R^8$ are independently selected from the group comprising of $C_1$-$C_4$ alkyl, $C_1$-$C_4$ haloalkyl, $C_3$-$C_6$ cycloalkyl or $C_3$-$C_6$ cycloalkyl-$C_1$-$C_4$ alkyl;

comprising one or more of the following steps a) to f):

a) reacting a substituted aniline of formula (II) with a trihaloacetonitrile of formula (IX) to obtain a compound of formula (Z), wherein $R^{10}$ is $CX_3$;

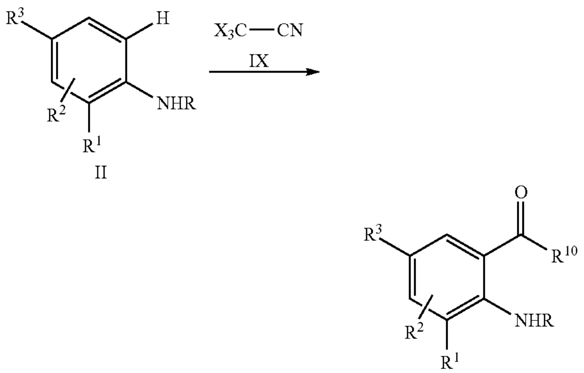

II

Z $R^{10}$ is $CX_3$ or i. reacting a substituted aniline of formula (II) with acetonitrile to obtain a substituted 2-aminoacetophenone compound of formula (III),

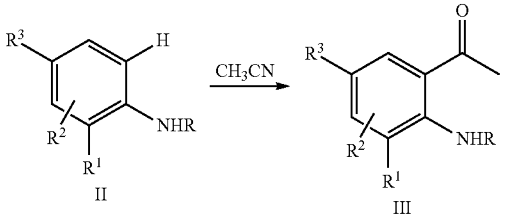

II

III and ii. halogenating the compound of formula (III) using a halogenating reagent to obtain a compound of formula (Z), wherein $R^{10}$ is $CX_3$;

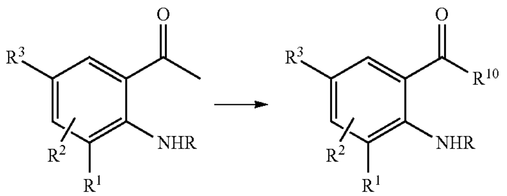

III

Z $R^{10}$ is $CX_3$ b) hydrolyzing the compound of formula (Z), wherein $R^{10}$ is $CX_3$, with a base or an acid to obtain a compound of formula (Z), wherein $R^{10}$ is $OR^9$ and $R^9$ is hydrogen and all other variables are as defined herein above;

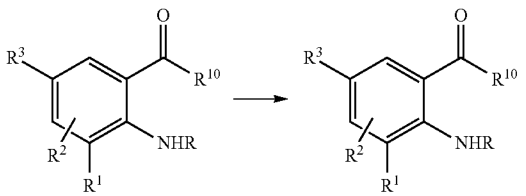

Z $R^{10}$ is $CX_3$

Z $R^{10}$ is $OR^9$ & $R^9$ is H or converting the compound of formula (III) to a compound of formula (Z), wherein $R^{10}$ is $OR^9$ and $R^9$ is hydrogen, without isolating the compound of formula (Z) wherein $R^{10}$ is $CX_3$;

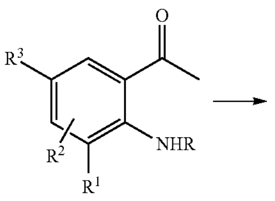

III

-continued

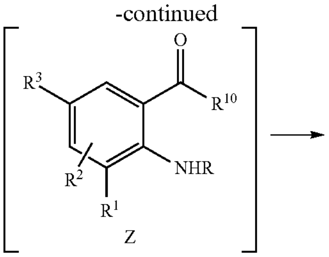

Z $R^{10}$ is $CX_3$

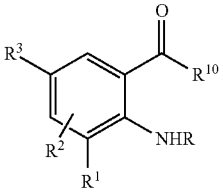

Z $R^{10}$ ia $OR^9$ & $R^9$ is H c) converting the compound of formula (Z), wherein $R^{10}$ is $CX_3$, to a compound of formula (Z), wherein $R^{10}$ is $OR^9$ and $R^9$ is alkyl and all other variables are as defined herein above; with a base or an acid and in the presence of an alcoholic solvent;

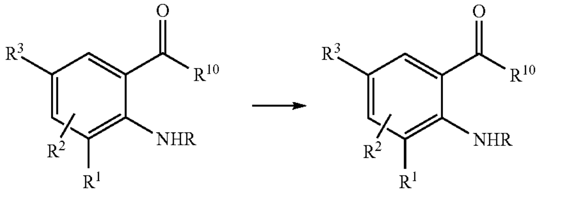

Z $R^{10}$ is $CX_3$

Z $R^{10}$ is $OR^9$ & $R^9$ is alkyl d) reacting the compound of formula (Z), wherein $R^{10}$ is $CX_3$, with a substituted amine of formula (VIII) to obtain a compound of formula (Z), wherein $R^{10}$ is $NR^{4a}R^{4b}$ and all other variables are as defined herein above;

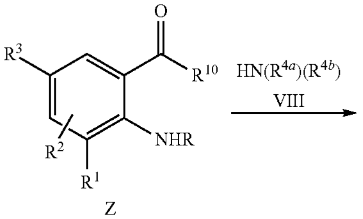

Z $R^{10}$ is $CX_3$

-continued

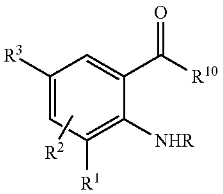

Z $R^{10}$ is $NR^{4a}R^{4b}$ e) reacting the compound of formula (Z), wherein $R^{10}$ is $OR^9$ and $R^9$ is hydrogen; with a substituted amine of formula (VIII) with a coupling reagent or a halogenating reagent and optionally in the presence of a base to obtain a compound of formula (Z), wherein $R^{10}$ is $NR^{4a}R^{4b}$ and all other variables are defined as herein above;

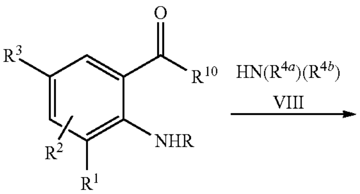

Z $R^{10}$ is $OR^9$ & $R^9$ is H

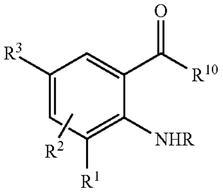

Z $R^{10}$ is $NR^{4a}R^{4b}$ or i. reacting the compound of formula (Z), wherein $R^{10}$ is $OR^9$ and $R^9$ is hydrogen, with an acid to obtain a compound of formula (IVa),

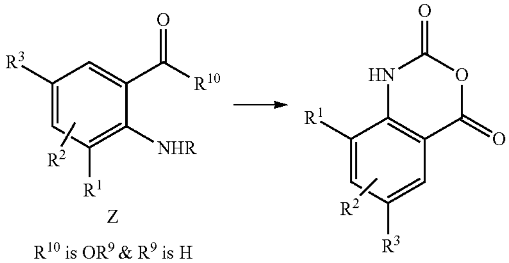

Z $R^{10}$ is $OR^9$ & $R^9$ is H

IVa and ii. reacting the compound of formula (IVa) with a substituted amine of formula (VIII) to obtain a compound of formula (Z), wherein $R^{10}$ is $NR^{4a}R^{4b}$ and all other variables are as defined herein above;

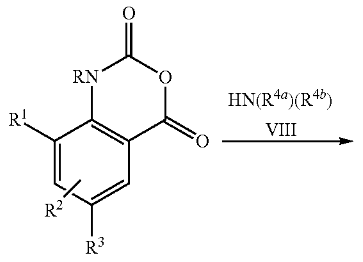

IVa

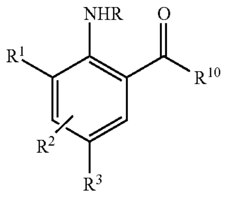

Z
$R^{10}$ is $NR^{4a}R^{4b}$ f) reacting the compound of formula (Z), wherein $R^{10}$ is $OR^9$ and $R^9$ is alkyl, with a substituted amine of formula (VIII) in the presence of a base to obtain a compound of formula (Z), wherein $R^{10}$ is $NR^{4a}R^{4b}$ and all other variables are as defined herein above;

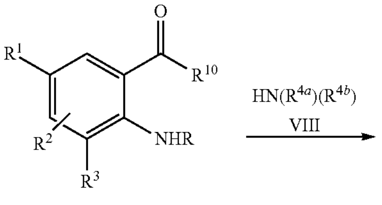

Z
$R^{10}$ is $OR^9$ & $R^9$ is alkyl

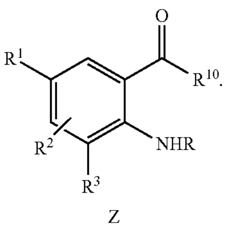

Z
$R^{10}$ is $NR^{4a}R^{4b}$

In another aspect of the present invention further relates to the process for the preparation of a compound of formula (I) or salts thereof, Formula (I)

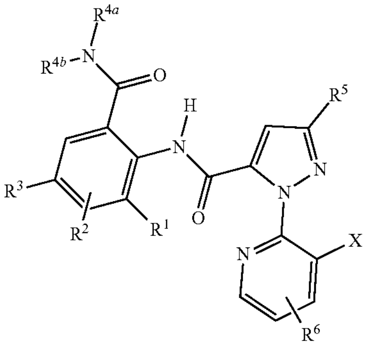

wherein, $R^1$ and $R^2$ are independently selected from the group comprising of hydrogen, halogen, $C_1$-$C_4$ alkyl, $C_1$-$C_4$ haloalkyl or $C_3$-$C_6$ cycloalkyl;

$R^3$ is selected from the group comprising of hydrogen, halogen, cyano, $C_1$-$C_4$ haloalkyl or $C_3$-$C_6$ cycloalkyl;

$R^{4a}$ and $R^{4b}$ are independently selected from the group comprising of hydrogen, $C_1$-$C_4$ alkyl, $C_3$-$C_6$ cycloalkyl, $C_3$-$C_6$ cycloalkyl-$C_1$-$C_4$ alkyl; or $NR^{4a}R^{4b}$ represents —N═S($R^7R^8$)═(O)$_n$, wherein $R^7$ and $R^8$ are independently selected from the group comprising of $C_1$-$C_4$ alkyl, $C_1$-$C_4$ haloalkyl, $C_3$-$C_6$ cycloalkyl or $C_3$-$C_6$ cycloalkyl $C_1$-$C_4$ alkyl;

n represents an integer from 0-1;

$R^5$ is selected from the group comprising of halogen, $C_1$-$C_4$ alkyl, $C_1$-$C_4$ haloalkyl, $CHF_2$, $CF_3$, $C_1$-$C_4$ alkoxy, $OCHF_2$, $OCH_2CF_3$, or -A-$C_3$-$C_5$ heterocyclyl;

wherein -A- is selected from the group comprising of direct bond, $CHR^6$, —O— or —S—; and said heterocyclyl may optionally be substituted with one or more group selected from hydrogen, halogen, cyano, $C_1$-$C_4$ alkyl or $C_1$-$C_4$ haloalkyl;

$R^6$ is selected from the group comprising of hydrogen, halogen, cyano, $C_1$-$C_4$ alkyl or $C_1$-$C_4$ haloalkyl;

and

X represents halogen;

comprising the step of reacting a substituted anthranilic amide of formula (Z),

Z

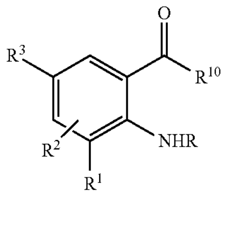

wherein $R^{10}$ is $NR^{4a}R^{4b}$ and wherein $R^1$ and $R^2$ are independently selected from the group comprising of hydrogen, halogen, $C_1$-$C_4$ alkyl, $C_1$-$C_4$ haloalkyl or $C_3$-$C_6$ cycloalkyl;

$R^3$ is selected from the group comprising of hydrogen, halogen, cyano, $C_1$-$C_4$ haloalkyl or $C_3$-$C_6$ cycloalkyl;

$R^{4a}$ and $R^{4b}$ are independently selected from the group comprising of hydrogen, $C_1$-$C_4$ alkyl, $C_3$-$C_6$ cycloalkyl-$C_1$-$C_4$ alkyl; or $NR^{4a}R^{4b}$ represents —N═S($R^7R^8$)═(O)$_n$, wherein $R^7$ and $R^8$ are independently selected from the group comprising of $C_1$-$C_4$ alkyl, $C_1$-$C_4$ haloalkyl $C_3$-$C_6$ cycloalkyl or $C_3$-$C_6$ cycloalkyl $C_1$-$C_4$ alkyl;

n represents an integer from 0-1;

with a pyrazole acid of formula (VII)

VII

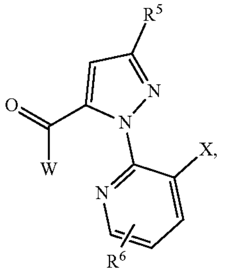

wherein W is OH, Cl, O—$C_1$-$C_4$ alkyl, O—C(O)$C_1$-$C_4$ alkyl or imidazolyl;

$R^5$ is selected from the group comprising of halogen, $C_1$-$C_4$ alkyl, $C_1$-$C_4$ haloalkyl, $CHF_2$, $CF_3$, $C_1$-$C_4$ alkoxy, $OCF_2H$, $OCH_2CF_3$, or -A-$C_3$-$C_5$ heterocyclyl;

wherein -A- is selected from the group comprising of direct bond, $CHR^6$, —O— or —S—; and said heterocyclyl may optionally be substituted with one or more group selected from hydrogen, halogen, cyano, $C_1$-$C_4$ alkyl or $C_1$-$C_4$ haloalkyl;

$R^6$ is selected from the group comprising of hydrogen, halogen, cyano, $C_1$-$C_4$ alkyl or $C_1$-$C_4$ haloalkyl and X represents halogen;

optionally in the presence of a base, a suitable reagent and a suitable solvent, according to the reaction scheme-1 as depicted below Scheme-1

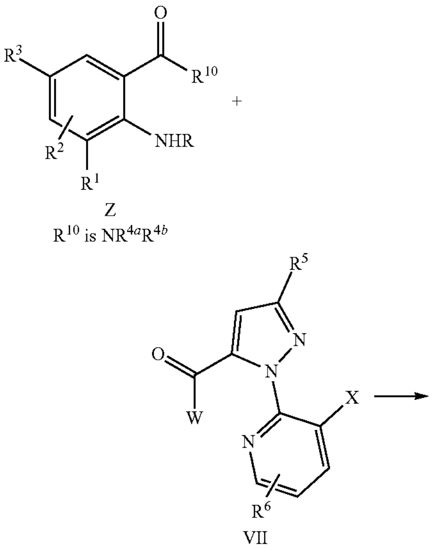

-continued

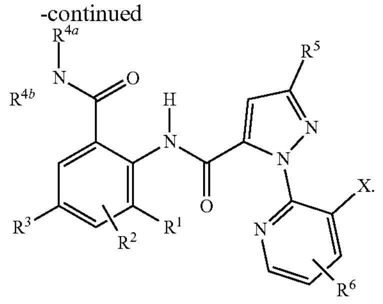

I

Further the compound of formula (Z) wherein $R^{10}$ is $NR^{4a}R^{4b}$ is obtained by one or more of the following steps:

a) reacting a substituted aniline of formula (II) with a trihaloacetonitrile of formula (IX) to obtain a compound of formula (Z), wherein $R^{10}$ is $CX_3$ and all other variables are defined herein above;

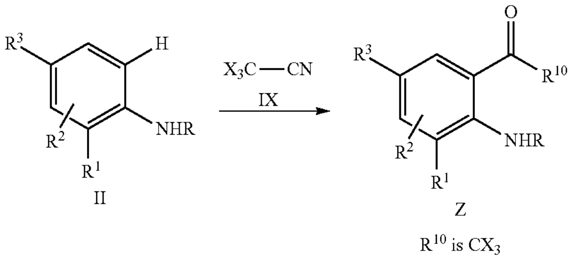

or i. reacting a substituted aniline compound of formula (II) with acetonitrile to obtain a substituted 2-aminoacetophenone of formula (X),

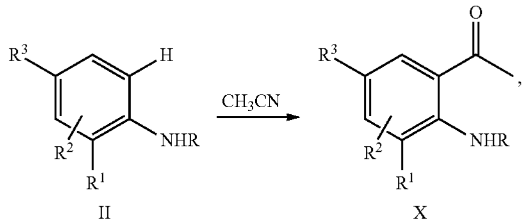

and ii. halogenating the compound of formula (III) using a halogenating reagent to obtain a compound of formula (Z), wherein $R^{10}$ is $CX_3$ and all other variables are defined herein above;

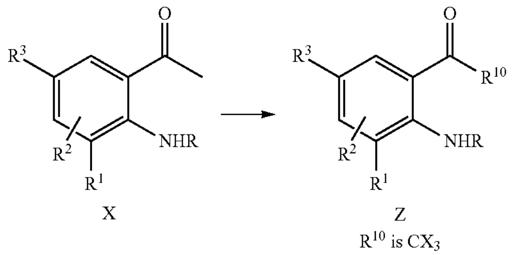

b) hydrolyzing the compound of formula (Z), wherein $R^{10}$ is $CX_3$, with a base or an acid to obtain a compound of formula (Z), wherein $R^{10}$ is $OR^9$ and $R^9$ is hydrogen and all other variables are defined herein above;

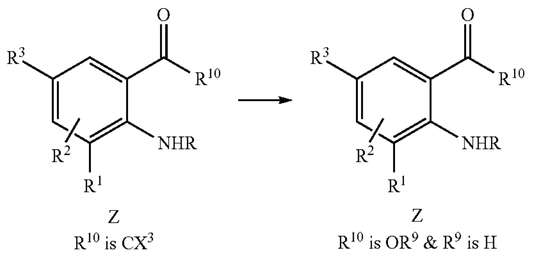

Z $R^{10}$ is $CX^3$ — Z $R^{10}$ is $OR^9$ & $R^9$ is H or converting the compound of formula (III) to a compound of formula (Z), wherein $R^{10}$ is $OR^9$ and $R^9$ is hydrogen, without isolation of the compound of formula (Z) wherein $R^{10}$ is $CX_3$ and all other variables are defined herein above;

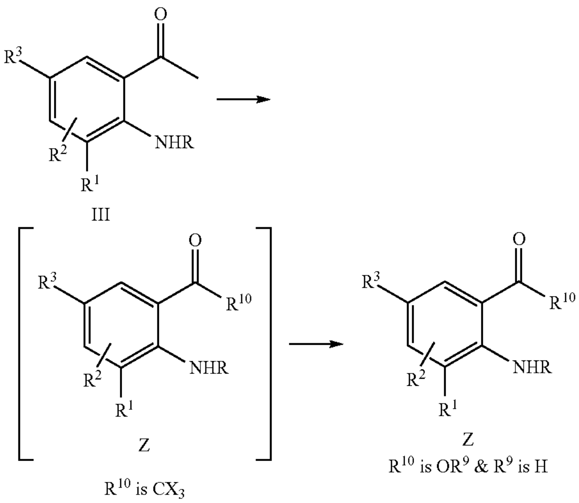

III

Z $R^{10}$ is $CX_3$ — Z $R^{10}$ is $OR^9$ & $R^9$ is H c) converting the compound of formula (Z), wherein $R^{10}$ is $CX_3$, to a compound of formula (Z), wherein $R^{10}$ is $OR^9$ and $R^9$ is alkyl and all other variables are defined herein above; with a base or an acid and in the presence of an alcoholic solvent;

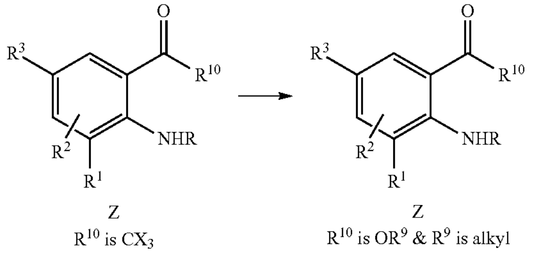

Z $R^{10}$ is $CX_3$ — Z $R^{10}$ is $OR^9$ & $R^9$ is alkyl d) reacting the compound of formula (Z), wherein $R^{10}$ is $CX_3$, with a substituted amine of formula (VIII) to obtain a compound of formula (Z), wherein $R^{10}$ is $NR^{4a}R^{4b}$ and all other variables are defined herein above;

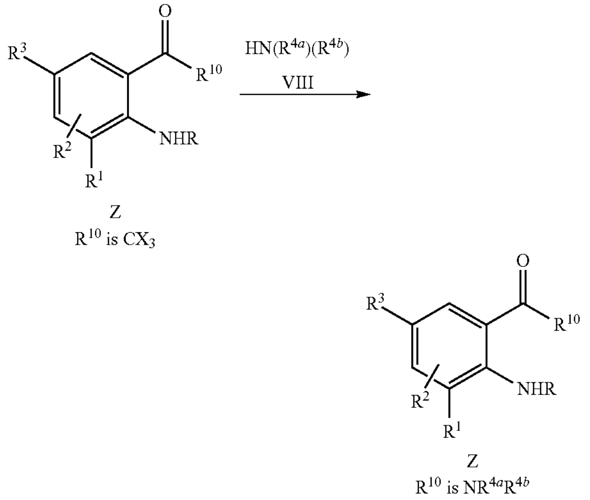

Z $R^{10}$ is $CX_3$ — Z $R^{10}$ is $NR^{4a}R^{4b}$ e) reacting the compound of formula (Z), wherein $R^{10}$ is $OR^9$ and $R^9$ is hydrogen; with a substituted amine of formula (VIII) in the presence of a coupling reagent or a halogenating reagent and optionally in the presence of a base to obtain a compound of formula (Z), wherein $R^{10}$ is $NR^{4a}R^{4b}$ and all other variables are defined herein above;

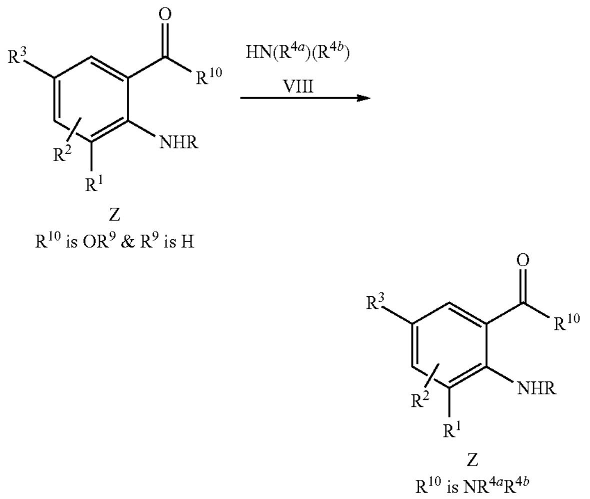

Z $R^{10}$ is $OR^9$ & $R^9$ is H — Z $R^{10}$ is $NR^{4a}R^{4b}$ or i. reacting the compound of formula (Z), wherein $R^{10}$ is $OR^9$ and $R^9$ is hydrogen; with an acid to obtain a compound of formula (IVa),

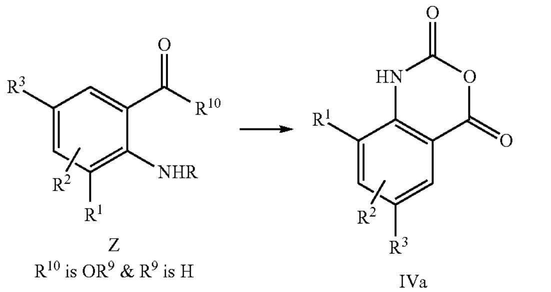

Z $R^{10}$ is $OR^9$ & $R^9$ is H — IVa and ii. reacting the compound of formula (IVa) with a substituted amine of formula (VIII) to obtain a compound of formula (Z), wherein $R^{10}$ is $NR^{4a}R^{4b}$ and all other variables are defined herein above;

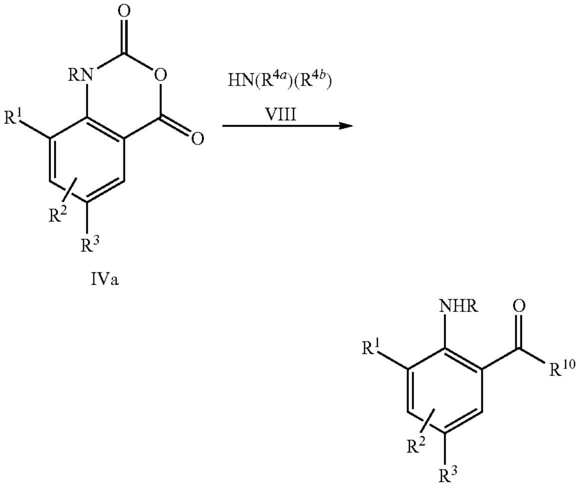

IVa

Z $R^{10}$ is $NR^{4a}R^{4b}$ f) reacting the compound of formula (Z), where in $R^{10}$ is $OR^9$ and $R^9$ is $C_1$-$C_4$ alkyl; with a substituted amine of formula (VIII) in the presence of a base to obtain a compound of formula (Z), wherein $R^{10}$ is $NR^{4a}R^{4b}$ and all other variables are defined herein above;

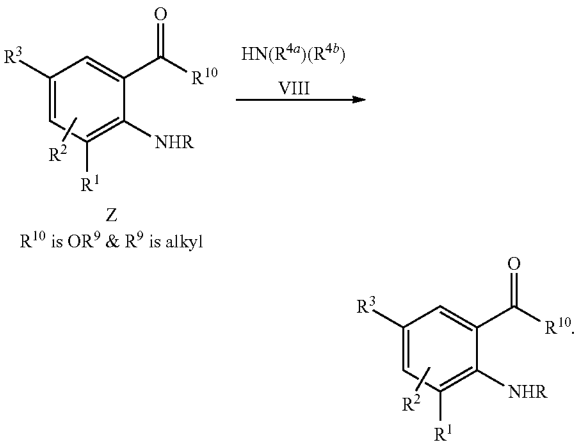

Z $R^{10}$ is $OR^9$ & $R^9$ is alkyl

Z $R^{10}$ is $NR^{4a}R^{4b}$

The compound of formula (VII) can be synthesized by using any of the methods known in the prior art. For instance the process for synthesis of compound of formula (VII) is disclosed in WO2003015518, WO20030155519, WO2011157664 and WO2013030100.

The compound of formula (Z) wherein $R^{10}$ is $NR^{4a}R^{4b}$ can be converted into the compound of formula (I) by using any of the suitable methods known in the prior art. For instance, the process for converting a compound of formula (Z) wherein $R^{10}$ is $NR^{4a}R^{4b}$ into a compound of formula (I) is disclosed in WO2006062978, WO2008010897 and WO2012103436.

In one aspect, the present invention provides a process for the synthesis of compounds of formula (Z), wherein $R^{10}$ is $CX_3$ and all other variables are as defined herein above, comprising reacting a substituted aniline of formula (II) with a trihaloacetonitrile of formula (IX) to obtain a compound of formula (Z), wherein $R^{10}$ is $CX_3$ and all other variables are as defined herein above;

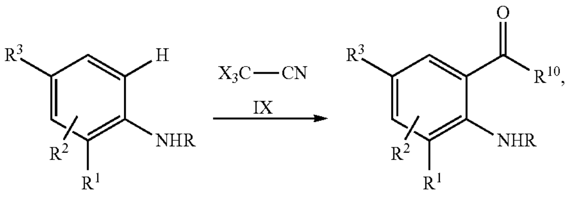

II

Z $R^{10}$ is $CX_3$ or i. reacting a substituted aniline of formula (II) with acetonitrile to obtain a substituted 2-aminoacetophenone of formula (X),

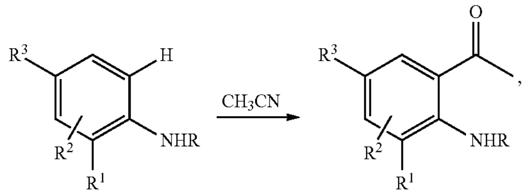

II

X and ii. halogenating the compound of formula (III) using a halogenating reagent to obtain a compound of formula (Z), wherein $R^{10}$ is $CX_3$ and all other variables are as defined herein above.

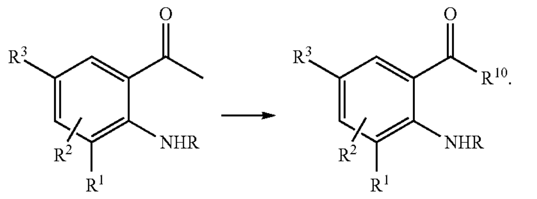

III

Z $R^{10}$ is $CX_3$

In another aspect, the present invention provides a process for the synthesis of a compound of formula (Z), wherein $R^{10}$ is $OR^9$ and $R^9$ is hydrogen, and all other variables are defined as herein above; comprising hydrolyzing the compound of formula (Z), wherein $R^{10}$ is $CX_3$, with a base or an acid to obtain a compound of formula (Z), wherein $R^{10}$ is $OR^9$; and $R^9$ is hydrogen and all other variables are as defined herein above;

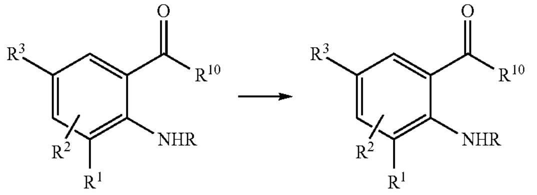

Z
$R^{10}$ is $CX^3$

Z
$R^{10}$ is $OR^9$ & $R^9$ is H or converting the compound of formula (III) to a compound of formula (Z), wherein $R^{10}$ is $OR^9$ and $R^9$ is hydrogenhydrogen, without isolating the compound of formula (Z), wherein $R^{10}$ is $CX_3$;

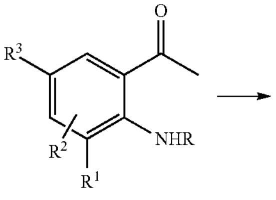

III

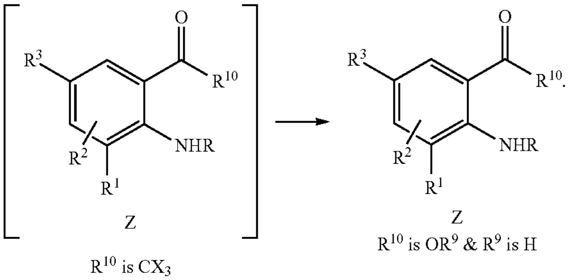

Z
$R^{10}$ is $CX_3$

Z
$R^{10}$ is $OR^9$ & $R^9$ is H

In yet another aspect, the present invention provides a process for the synthesis of a compound of formula (Z), wherein $R^{10}$ is $OR^9$ and $R^9$ is hydrogen, and all other variables are as defined herein above comprising converting the compound of formula (III) to a compound of formula (Z), wherein $R^{10}$ is $OR^9$; and $R^9$ is hydrogen and all other variables are as defined herein above, without isolating the compound of formula (Z), wherein $R^{10}$ is $CX_3$;

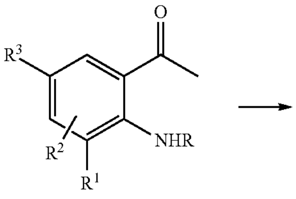

III

-continued

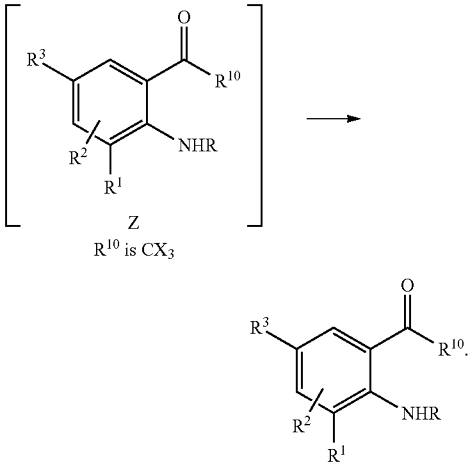

Z
$R^{10}$ is $CX_3$

Z
$R^{10}$ is $OR^9$
& $R^9$ is H

In yet another aspect, the present invention provides a process for the synthesis of a compound of formula (Z), wherein $R^{10}$ represents $OR^9$ and $R^9$ is $C_1$-$C_4$ alkyl and all other variables are as defined herein above comprising converting the compound of formula (Z), wherein $R^{10}$ is $CX_3$, to a compound of formula (Z), wherein $R^{10}$ is $OR^9$ and $R^9$ is alkyl and all other variables are defined as herein above; with a base or an acid and in the presence of an alcoholic solvent.

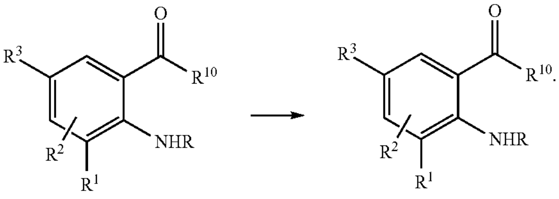

Z
$R^{10}$ is $CX_3$

Z
$R^{10}$ is $OR^9$
& $R^9$ is alkyl

In yet another aspect, the present invention provides a process for the synthesis of a compound of formula (Z), wherein $R^{10}$ represents $OR^9$ and $R^9$ is $C_1$-$C_4$ alkyl and all other variables are as defined herein above; from a compound of formula (X) comprising, converting the compound of formula (III) to a compound of formula (Z), wherein $R^{10}$ is $OR^9$; and $R^9$ is $C_1$-$C_4$ alkyl, without isolation of the compound of formula (Z) wherein $R^{10}$ is $CX_3$.

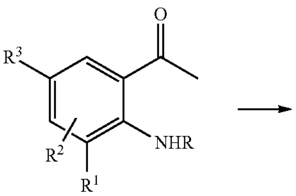

III

-continued

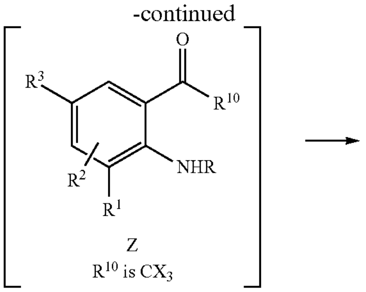

Z
$R^{10}$ is $CX_3$

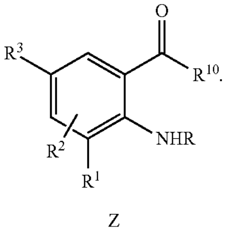

Z
$R^{10}$ is $OR^9$ & $R^9$ is $C_1$—$C_4$ alkyl

In yet another aspect, the present invention provides a process for the synthesis of a compound of formula (Z), wherein $R^{10}$ is $NR^{4a}R^{4b}$ and all other variables are as defined herein above;

comprising, reacting the compound of formula (Z), wherein $R^{10}$ is $CX_3$, with a substituted amine of formula (VIII) to obtain a compound of formula (Z), wherein $R^{10}$ is $NR^{4a}R^{4b}$;

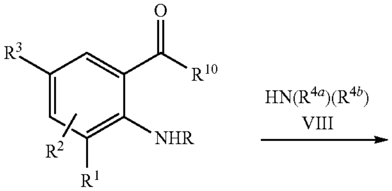

Z
$R^{10}$ is $CX_3$

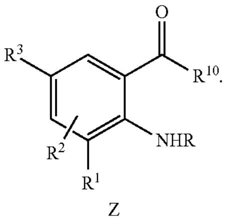

Z
$R^{10}$ is $NR^{4a}R^{4b}$

In yet another aspect, the present invention provides a process for the synthesis of a compound of formula (Z), wherein $R^{10}$ is $NR^{4a}R^{4b}$ and all other variables are as defined herein above; comprising, reacting the compound of formula (Z), wherein $R^{10}$ is $OR^9$ and $R^9$ is hydrogen; with a substituted amine of formula (VIII) with a coupling reagent or a halogenating reagent and optionally in the presence of a base to obtain a compound of formula (Z), wherein $R^{10}$ is $NR^{4a}R^{4b}$;

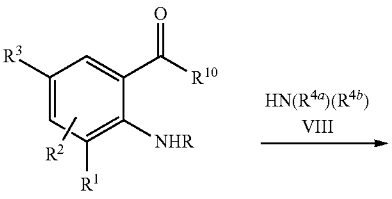

Z
$R^{10}$ is $OR^9$ &
$R^9$ is H

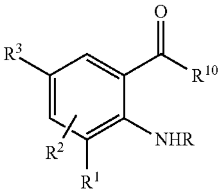

Z
$R^{10}$ is $NR^{4a}R^{4b}$ or i. reacting the compound of formula (Z), wherein $R^{10}$ is $OR^9$ and $R^9$ is hydrogen; with an acid to obtain a compound of formula (IVa),

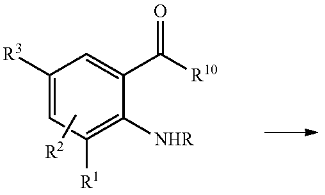

Z
$R^{10}$ is $OR^9$ &
$R^9$ is H

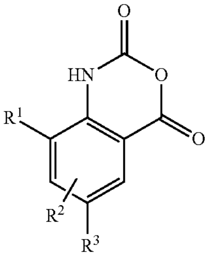

IVa and ii. reacting the compound of formula (IVa) with a substituted amine of formula (VIII) to obtain a compound of formula (Z), wherein $R^{10}$ is $NR^{4a}R^{4b}$,

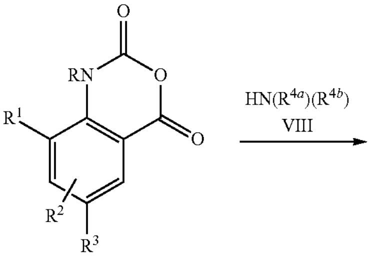

IVa

-continued

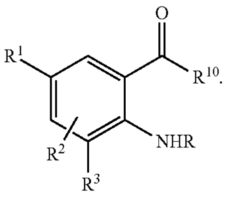

Z
$R^{10}$ is $NR^{4a}R^{4b}$

In yet another aspect, the present invention provides a process for the synthesis of a compound of formula (Z) wherein $R^{10}$ is $NR^4R^{4b}$ and all other variables are as defined herein above; comprising, reacting the compound of formula (Z), wherein $R^{10}$ is $OR^9$ and $R^9$ is alkyl; with a substituted amine of formula (VIII) in the presence of a base to obtain a compound of formula (Z), wherein $R^{10}$ is $NR^{4a}R^{4b}$;

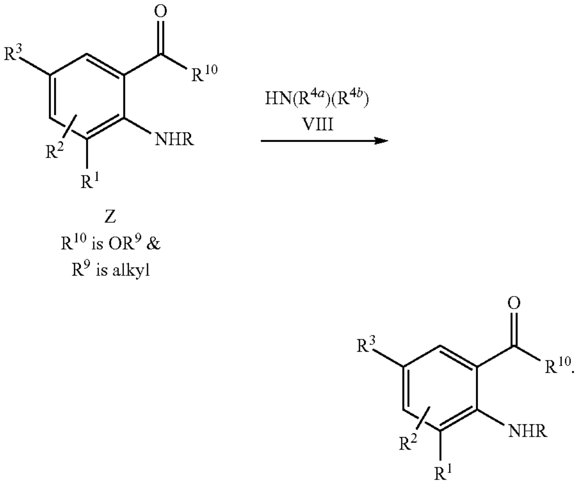

Z
$R^{10}$ is $OR^9$ &
$R^9$ is alkyl

Z
$R^{10}$ is $NR^{4a}R^{4b}$

In another aspect, the present invention provides a process for the synthesis of a compound of formula (Z), wherein $R^{10}$ is $OR^9$ and $R^9$ is hydrogen, and all other variables are defined as herein above; comprising, hydrolyzing the compound of formula (Z), wherein $R^{10}$ is $OR^9$ and $R^9$ is $C_1$-$C_4$ alkyl, with a base or an acid to obtain a compound of formula (Z), wherein $R^{10}$ is $OR^9$, and $R^9$ is hydrogen and all other variables are as defined herein above;

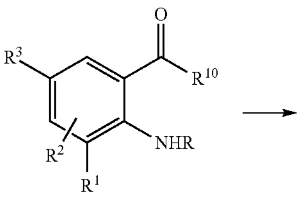

Z
$R^{10}$ is $OR^9$ & $R^9$ is
$C_1$—$C_4$ alkyl

-continued

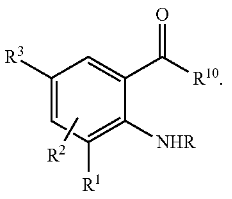

Z
$R^{10}$ is $OR^9$ &
$R^9$ is H

In another aspect, the present invention provides a process for the synthesis of a compound of formula (Z), wherein $R^{10}$ is $CX_3$, and $R^3$ is halogen, from compound of formula (III), wherein $R^3$ is hydrogen, and all other variables are defined as herein above;

comprising, halogenating the compound of formula (III), wherein $R^3$ is hydrogen, using a halogenating reagent to obtain a compound of formula (Z), wherein $R^{10}$ is $CX_3$ and $R^3$ is halogen;

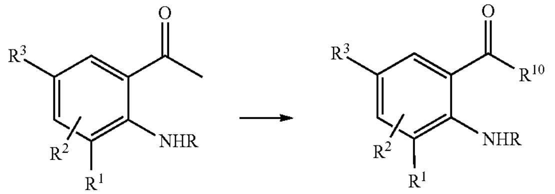

III
$R^3$ is H

Z
$R^{10}$ is $CX_3$ and
$R^3$ is X and all other variables are as defined herein above.

In yet another aspect, the present invention provides a process for the synthesis of a compound of formula (I); comprising, reacting the compound of formula (Z), wherein $R^{10}$ is $NR^{4a}R^{4b}$ with a compound of formula (VII) wherein, W is OH, Cl, O—$C_1$-$C_4$ alkyl, O—C(O)$C_1$-$C_4$ alkyl or imidazolyl; to obtain the compound of formula (I), wherein all variables are as defined herein above,

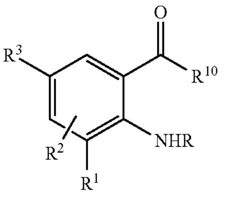

Z
$R^{10}$ is $NR^{4a}R^{4b}$

+

-continued

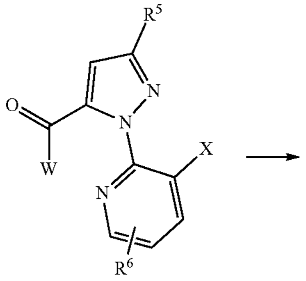

VII

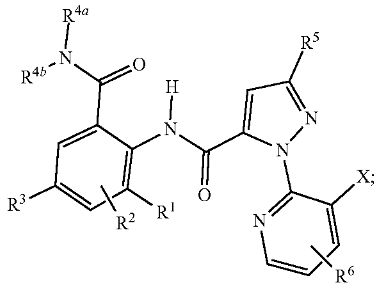

I or i. reacting the compound of formula (Z), wherein $R^{10}$ is $OR^9$ and $R^9$ is hydrogen, with a compound of formula (VII), to obtain a compound of formula (IA),

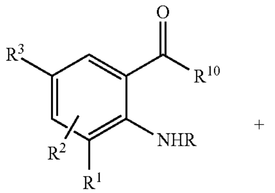

Z
$R^{10}$ is $OR^9$ &
$R^9$ is H

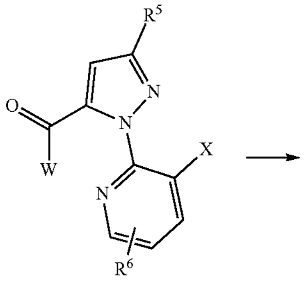

VII

-continued

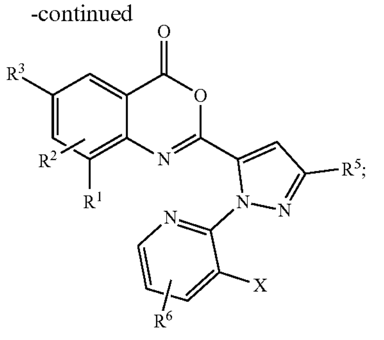

IA and ii. reacting the compound of formula (IA) with a substituted amine of formula (VIII) to obtain a compound of formula (I);

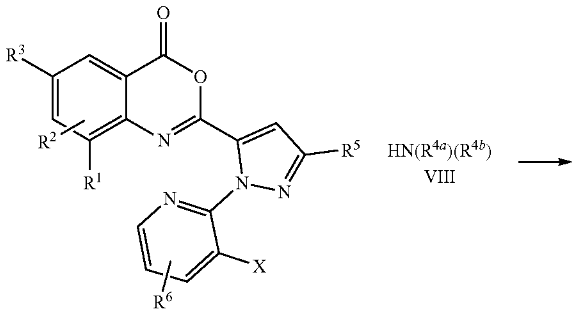

IA

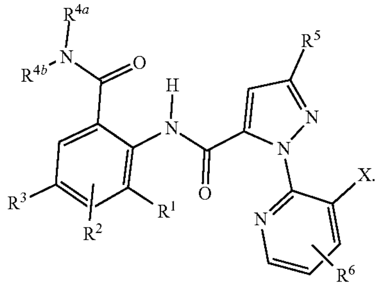

I

In one embodiment the compound of formula (IVa) is prepared from a compound of formula (Z) wherein R is hydrogen, $R^{10}$ is $OR^9$ and $R^9$ is hydrogen, using triphosgene.

In another aspect, the present invention provides a compound of formula (Z) or a salt thereof, Formula (Z)

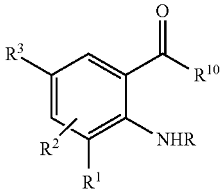

wherein, $R^1$ and $R^2$ are independently selected from the group comprising of hydrogen, halogen, $C_1$-$C_4$ alkyl, $C_1$-$C_4$ haloalkyl or $C_3$-$C_6$ cycloalkyl;

$R^3$ is selected from the group comprising of hydrogen, halogen, cyano, $C_1$-$C_4$ haloalkyl or $C_3$-$C_6$ cycloalkyl;

R is selected from the group comprising of hydrogen or $COR^{11}$;

wherein, $R^{11}$ is selected from the group comprising of $C_1$-$C_4$ alkoxy, O-benzyl or O-phenyl;

$R^{10}$ represents $CX_3$;

X represents chloro or bromo; with the proviso that the compounds 1-(2-amino-5-chlorophenyl)-2,2,2-trichloroethan-1-one and 1-(2-amino-5-fluorophenyl)-2,2,2-trichloroethan-1-one, are excluded from the compounds of formula (Z).

In a preferred embodiment, the present invention provides the process for synthesis of a compound of formula (Z), Formula (Z)

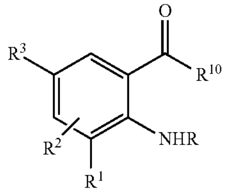

wherein, $R^1$ is methyl or halogen; more preferably $R^1$ is methyl, chloro or bromo;

$R^2$ is hydrogen or halogen; more preferably $R^2$ is hydrogen or fluoro;

$R^3$ is halogen or cyano; more preferably $R^3$ is chloro, bromo or cyano;

$R^1$ is $CX_3$, $OR^9$ or $NR^{4a}R^{4b}$;

$R^{4a}$ is methyl, ethyl, n-propyl, iso-propyl, cyclopropyl methylcyclopropyl, ethylcyclopropyl, iso-butyl, tert-butyl; $R^{4b}$ is hydrogen or methyl, X is halogen; more preferably chloro or bromo;

$R^9$ hydrogen, methyl, ethyl n-propyl, iso-propyl, iso-butyl, tert-butyl.

In one embodiment, the compound of formula (Z), wherein $R^{10}$ is $NR^{4a}R^{4b}$, is obtained from a compound of formula (Z), wherein $R^{10}$ is $CX_3$, without isolating compound of formula (Z), wherein $R^{10}$ is $OR^9$ and $R^9$ is hydrogen.

In yet another embodiment, the anthranilic acid of formula (Z), wherein $R^{10}$ is $OR^9$ and $R^9$ is hydrogen, is converted into the substituted anthranilic amide compound of formula (Z), wherein $R^{10}$ is $NR^{4a}R^{4b}$, by reacting the said anthranilic acid compound of formula (Z), wherein $R^{10}$ is $OR^9$ and $R^9$ is hydrogen, with a suitable amine of formula (VIII) [$HN(R^{4a})(R^{4b})$] wherein $R^{4a}$ and $R^{4b}$ are independently selected from hydrogen, $C_1$-$C_4$ alkyl or $C_3$-$C_6$ cycloalkyl-$C_1$-$C_4$ alkyl, in the presence of a suitable coupling reagent or a halogenating reagent.

In one embodiment, the present invention provides a process for the synthesis of a compound of formula (Z) wherein $R^3$ is bromo, chloro or cyano.

In one embodiment, the present invention provides a process for the synthesis of a compound of formula (Z) wherein $R^1$ is methyl, bromo or chloro.

In a preferred embodiment, the present invention provides a process for the synthesis of a compound of formula (Z) wherein $R^1$ is methyl or chloro.

In one embodiment, the present invention provides a process for the synthesis of a compound of formula (Z) wherein $R^1$ is methyl or chloro and $R^3$ is bromo, chloro or cyano.

In a preferred embodiment, the present invention provides the process for synthesis of a compound of formula (I), Formula (I)

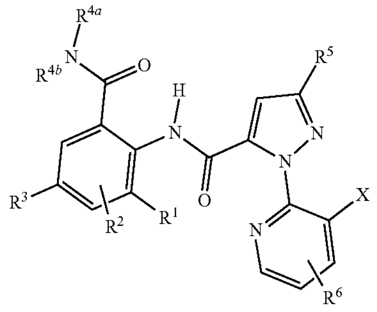

wherein, $R^1$ is methyl or halogen; more preferably $R^1$ is methyl, chloro or bromo;

$R^2$ is hydrogen or halogen; more preferably $R^2$ is hydrogen or fluoro;

$R^3$ is halogen or cyano; more preferably $R^3$ is chloro, bromo or cyano;

$R^{4a}$ is methyl, ethyl, n-propyl, iso-propyl, cyclopropyl methylcyclopropyl, ethylcyclopropyl, iso-butyl, tert-butyl; $R^{4b}$ is hydrogen or methyl, X is halogen; more preferably fluoro, chloro or bromo;

$R^5$ is bromo, chloro, $CF_3$, or -A-$C_3$-$C_5$ heterocyclyl;

wherein -A- is selected from the group comprising of direct bond, $CHR^6$, —O— or —S—; and said heterocyclyl may optionally be substituted with one or more group selected from hydrogen, halogen, cyano, $C_1$-$C_4$ alkyl or $C_1$-$C_4$ haloalkyl;

$R^6$ is selected from the group comprising of hydrogen, halogen, cyano, $C_1$-$C_4$ alkyl or $C_1$-$C_4$ haloalkyl.

In one embodiment, the present invention provides a process for the synthesis of a compound of formula (I) wherein $R^5$ is bromo or optionally substituted 3-5 membered heterocycle.

In preferred embodiment, the present invention provides a process for the synthesis of a compound of formula (I) wherein $R^5$ is bromo or optionally substituted 4-5 membered heterocycle.

In more preferred embodiment, the present invention provides a process for the synthesis of a compound of formula (I) wherein $R^5$ is bromo or optionally substituted 5 membered heterocycle.

In one more preferred embodiment, the present invention provides a process for the synthesis of a compound of formula (I) wherein $R^5$ is bromo or

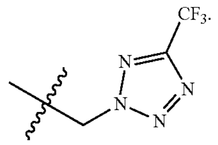 [SMILES: *Cn1nnc(C(F)(F)F)n1]

The suitable reagent used for amidation reactions for examples step e or converting anthranilic amide of formula (Z), wherein $R^{10}$ is $NR^{4a}R^{4b}$ reacting with compound of formula (VII) to obtain compound of formula (I) are a coupling reagent or a halogenating reagent.

In a preferred embodiment, the suitable coupling reagent is selected from but is not limited to 1-(3-dimethylaminopropyl)-3-ethylcarbodiimide hydrochloride (EDC), dicyclohexylcarbodiimide (DCC), 1-cyclohexyl-3-(2-morpholinoethyl)carbodiimide, 1,3-di-tert-butylcarbodiimide, 1-(dimethylaminopropyl)-3-ethylcarbodiimide methiodide, 1,3-diisopropylcarbodiimide, bis-(diphenylmethyl)-carbodiimide, 1-tert-butyl-3-ethylcarbodiimide, 1-methyl-2-chloropyridinium iodide, 2-ethoxy-1-ethoxycarbonyl-1,2-dihydroquinoline (EEDQ), BOP-chloride and isobutyl chloroformate.

In a preferred embodiment, a suitable halogenating reagent used for amidation reactions which include, but are not limited to, $SOCl_2$, $SO_2Cl_2$, $COCl_2$, $X_2$, $C(=O)(OCl_3)_2$, Chloramine-T, methanesulfonyl chloride, $POX_3$, $PX_3$, $PX_5$ or metal halides; wherein X is Cl or Br.

In yet another embodiment, the anthranilic ester compound of formula (Z) where in $R^{10}$ is $OR^9$ and $R^9$ is alkyl, is converted into a substituted anthranilic amide compound of formula (Z), wherein $R^{10}$ is $NR^{4a}R^{4b}$, by reacting the said anthranilic ester of formula (Z), wherein $R^{10}$ is $OR^9$ and $R^9$ is alkyl with a suitable amine of formula (VIII) $[HN(R^{4a})(R^{4b})]$ wherein $R^{4a}$ and $R^{4b}$ are independently hydrogen, $C_1$-$C_4$ alkyl or $C_3$-$C_6$ cycloalkyl-$C_1$-$C_4$ alkyl, optionally in the presence a suitable solvent and with a suitable base at a temperature within the range of 20° C. to 100° C.

The hydrolysis reaction is carried out by reacting a trihalo substituted phenylethanone compound of formula (Z), wherein $R^{10}$ is $CX_3$ in a suitable solvent with a suitable base or suitable acid and optionally in the presence of a suitable solvent at a temperature within the range of 0° C. to 120° C. to obtain an anthranilic acid of formula (Z), wherein $R^{10}$ is $OR^9$ and $R^9$ is hydrogen; or an anthranilic ester of formula (Z) where in $R^{10}$ is $OR^9$ and $R^9$ is alkyl.

Suitable bases being useful for converting a trihalo substituted phenylethanone of formula (Z), wherein $R^{10}$ is $CX_3$ into an anthranilic acid of formula (Z), wherein $R^{10}$ is $OR^9$ and $R^9$ is hydrogen; or into an anthranilic ester of formula (Z), wherein $R^{10}$ is $OR^9$ and $R^9$ is alkyl, include but are not limited to inorganic or organic bases.

Inorganic bases are preferably selected from the group comprising of ammonia, alkali or alkaline earth metal hydroxide, carbonate, bicarbonate and the like, wherein the alkali and alkaline earth metals are selected from the group comprising of lithium, sodium, potassium, rubidium, caesium, calcium, magnesium, barium and the like.

The organic bases are preferably selected from the group comprising of amines such as methylamine, dimethyl amine, diethyl amine, triethylamine, diisopropylamine, diisopropyl ethyl amine, pyridine, alkylated and dialkylated pyridines, dimethylamino pyridine, piperidine, DBU, DABCO, dicyclohexylethylamine, dicyclohexylmethylamine, and the like or mixtures thereof.

Suitable acids being useful for converting a trihalo substituted phenylethanone of formula (Z), wherein $R^{10}$ is $CX_3$ into an anthranilic acid of formula (Z), wherein $R^{10}$ is $OR^9$ and $R^9$ is hydrogen; or into an anthranilic ester of formula (Z), wherein $R^{10}$ is $OR^9$ and $R^9$ is alkyl, include but are not limited to inorganic acids such as hydrochloric acid, hydrobromic acid, sulfuric acid, and the like; organic acids such as formic acid, acetic acid, trifluoroacetic acid, propionic acid, methanesulfonic acid, benzenesulfonic acid, p-toluenesulfonic acid, and the like; or acidic ion-exchange resins or zeolithes.

In one embodiment, the conversion of a substituted aniline of formula (II) into a trihalo substituted phenylethanone of formula (Z), wherein $R^{10}$ is $CX_3$ or into a substituted 2-aminoacetophenone of formula (III) is carried out by reacting it with a suitable tri-halo compound of formula (IX) in the presence of one or more Lewis acid/s and optionally in the presence of a suitable solvent.

Suitable Lewis acids being useful for converting a substituted aniline of formula (II) into a trihalo substituted phenylethanone of formula (Z), wherein $R^{10}$ is $CX_3$ or into a substituted aniline of formula (III) include but are not limited to $AlX_3$, $BX_3$, $FeX_3$, $ZnX_2$, $GaX_3$, $InX_3$, $TiX_4$, $BiX_3$, $SbX_3$, $SnX_2$, $SnX_4$, $SiX_4$, hypovalent Lewis acids and the like wherein X is Cl, Br or I.

Preferred suitable Lewis acids for converting a substituted aniline of formula (II) into a trihalo substituted phenylethanone of formula (Z), wherein $R^{10}$ is $CX_3$ or into a substituted aniline of formula (III) include but are not limited to $AlX_3$, $BX_3$, $FeX_3$, and $GaX_3$, more preferably are $AlCl_3$ and $BCl_3$.

In one embodiment, the conversion of a substituted aniline of formula (II) into a trihalo substituted phenylethanone of formula (Z), wherein $R^{10}$ is $CX_3$, or into a substituted 2-aminoacetophenone of formula (III) is carried out by reacting it with a suitable trihalo compound of formula (IX) in the presence of one or more Lewis acid/s within a temperature range of −20° C. to 150° C.

The halogenation reaction is carried out by reacting the substituted aniline of formula (III) in a suitable solvent with bromine, chlorine or iodine in the presence or absence of sodium hypobromide and/or of sodium hypochloride at a temperature within the range of 0° C. to 100° C. for a period of 30 min to 2 h, to afford the trihalo substituted phenylethanone of formula (Z), wherein $R^{10}$ is $CX_3$.

The halogenations as described in the present invention are carried out in the presence of a suitable halogenating reagent which include, but are not limited to, HX, $SOCl_2$, $SO_2Cl_2$, $COCl_2$, $X_2$, $C(=O)(OCl_3)_2$, t-BuOCl, $NaOCl_1$, NaOBr Chloramine-T, N-halosuccinamides, N-halosaccharins, N-halohydantoines, methanesulfonyl chloride, $POX_3$, $PX_3$, $PX_5$ or metal halides; wherein X is Cl, Br or I.

The suitable acid useful for converting compound of formula (Z), wherein $R^{10}$ represent $OR^9$ and $R^9$ is hydrogen, to a compound of formula (IVa), includes but is not limited to an acid such as sulfuric acid, acetic acid, methanesulfonic acid, benzenesulfonic acid, p-toluenesulfonic acid, pyridinium p-toluenesulfonic acid (PPTS) and the like; or acidic ion-exchange resins or Zeolithes and the like.

The suitable solvents as used in any of the process steps of the present invention are selected from aliphatic, alicyclic or aromatic hydrocarbons such as, petroleum ether, hexane, heptane, cyclohexane, methylcyclohexane, toluene, xylene or decalin; aliphatic, alicyclic or aromatic halogenated hydrocarbons such as chlorobenzene, dichlorobenzene, dichloromethane, chloroform, tetrachloromethane, dichloroethane or trichloroethane; ethers such as diethylether, diisopropyl ether, methyl tert-butyl ether, methyl tert-amyl ether, dioxane, tetrahydrofuran, 1,2-dimethoxy ethane, 1,2-diethoxyethane or anisole; nitriles such as acetonitrile, propionitrile, n- or iso-butyronitrile or benzonitrile; amides such as N,N-dimethylformamide, N,N-dimethylacetamide, N-methyl formanilide, N-methylpyrrolidone or hexamethylphosphoric triamide; sulfoxides such as dimethyl sulfoxide or sulfones such as sulfolane; alcohols such as methanol, ethanol, isopropanol, polyethylene glycols; water or mixtures thereof.

The preferred solvents used for acylation or trihaloacylation (Step-a and step-a-i)) are aliphatic, alicyclic or aromatic halogenated hydrocarbons such as chlorobenzene, dichlorobenzene, dichloromethane, chloroform, tetrachloromethane, dichloroethane, trichloroethane, toluene or sulfolane.

The preferred solvents used for halogenation reaction (Step-a-ii) are aliphatic, alicyclic or aromatic halogenated hydrocarbons such chlorobenzene, dichlorobenzene, dichloromethane, chloroform, tetrachloromethane, dichloroethane, trichloroethane or acetic acid.

The preferred solvents used for hydrolysis reaction (Step-b) are ethers such as diethylether, diisopropyl ether, methyl tert-butyl ether, methyl tert-amyl ether, dioxane, tetrahydrofuran, 1,2-dimethoxy ethane, 1,2-diethoxyethane; nitriles such as acetonitrile, propionitrile, n- or iso-butyronitrile or benzonitrile; water or mixtures thereof.

The solvents used for reaction Step-c, are alcohols such as methanol, ethanol, isopropanol, and the like.

The preferred solvents used for amidation reactions (Step-d, e or f) are all inert organic solvents. These preferably include aliphatic, alicyclic or aromatic hydrocarbons such as, petroleum ether, hexane, heptane, cyclohexane, methylcyclohexane, toluene, xylene or decalin; aliphatic, alicyclic or aromatic halogenated/as chlorobenzene, dichlorobenzene, dichloromethane, chloroform, tetrachloromethane, dichloroethane or trichloroethane; ethers such as diethylether, diisopropyl ether, methyl tert-butyl ether, methyl tert-amyl ether, dioxane, tetrahydrofuran, 1,2-dimethoxy ethane, 1,2-diethoxyethane or anisole; nitriles such as acetonitrile, propionitrile, n- or iso-butyronitrile or benzonitrile; amides such as N,N-dimethylformamide, N,N-dimethylacetamide, N-methyl formanilide, N-methylpyrrolidone or hexamethylphosphoric triamide; sulfoxides such as dimethyl sulfoxide or sulfones such as sulfolane;

In one embodiment, the present invention provides a process for the synthesis of compound of formula (I) wherein, the compound of formula (I) includes chlorantraniliprole, cyantraniliprole, cyclaniliprole, tetraniliprole, tetra-chlorantraniliprole, bromoantraniliprole, dichlorantraniliprole and fluchlordiniliprole.

The processes as disclosed in the present invention are preferably carried out batch-wise. However, semi-continuous or continuous reaction passages are also possible.

The processes as disclosed in the present invention can be run in the absence of a solvent or in the presence of one or more suitable solvent. The optional solvent should be resistant against oxidation (i.e. a solvent will be preferred whose rate of oxidation is substantially lower than that of the compounds of formula I to VII) and suitable for suspending, or preferably dissolving the reactants.

Any person skilled in the art knows the best work-up of the reaction mixtures after the end of the respective reactions. In one embodiment, the work-up is usually carried out by isolation of the product by filtration, and optionally washing with solvent, further optionally drying of the product if required.

The process steps according to the invention are generally carried out under atmospheric pressure. Alternatively, however, it is also possible to carry out the reaction under increased or reduced pressure.

Without further elaboration, it is believed that any person skilled in the art who is using the preceding description can utilize the present invention to its fullest extent. The following examples are therefore to be interpreted as merely illustrative and not limiting of the disclosure in any way whatever.

EXAMPLES

Example-1: Synthesis of 1-(2-amino-5-chloro-3-methylphenyl)ethan-1-one

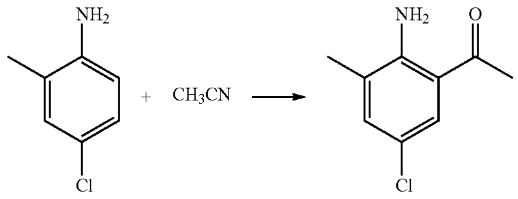

(1) (2)

To a suspension of aluminium trichloride (1.130 g, 8.47 mmol) and anhydrous toluene (10 mL) that was cooled in an ice-bath under nitrogen atmosphere, a solution of 4-chloro-2-methylaniline (0.840 mL, 7.06 mmol) in toluene (5 mL) was added drop wise under stirring. To this stirred reaction mixture, a 1 M solution of boron trichloride in dichloromethane (7.77 mL, 7.77 mmol) was added drop wise over a period of 15 minutes. To this reaction mixture, acetonitrile (2.4 mL, 45.96 mmol) was added over a period of 15 minutes and stirring was continued for further 10 minutes. The reaction mixture was heated gradually to 85° C. and maintained at this temperature for 36 h. After completion of the reaction, the reaction mixture was cooled to room temperature followed by the addition of water (4 mL). The reaction mixture was then refluxed for 1 h, subsequently cooled to room temperature and extracted with ethyl acetate (2×20 mL). The combined organic layers were washed with water, dried over anhydrous sodium sulphate and concentrated under reduced pressure to obtain a crude product. The crude product was purified with flash chromatography to obtain 1-(2-amino-5-chloro-3-methylphenyl)ethan-1-one.

$^1$H NMR (400 MHz, $CDCl_3$) δ2.15 (s, 3H), 2.57 (s, 3H), 7.16-7.17 (m, 1H), 7.58 (d, J=2.4 Hz, 1H)

Example-2: Synthesis of 1-(2-amino-3-methylphenyl)ethan-1-one

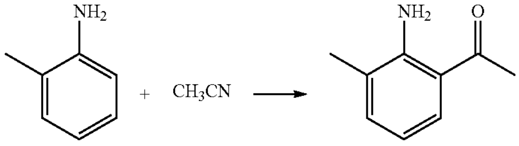

(6) (7)

A solution of anhydrous toluene (15 mL) and o-toluidine (0.996 mL, 9.33 mmol) was cooled in an ice-bath under nitrogen atmosphere. To this solution, a 1 M solution of boron trichloride in dichloromethane (10.27 mL, 10.27 mmol) was added drop wise over a period of 15 minutes under stirring. To this reaction mixture, acetonitrile (2.92 mL, 56.0 mmol) was added over a period of 15 minutes, followed by the addition of aluminium chloride (1.493 g, 11.20 mmol). The reaction mixture was stirred for further 10 minutes, and then heated gradually to 85° C. and maintained at this temperature for 16 h. After completion of the reaction, the reaction mixture was cooled to room temperature, followed by the addition of water (4 mL) and by extraction with ethyl acetate (2×20 mL). The combined organic layers were washed with water, dried over anhydrous sodium sulphate and concentrated under reduced pressure to obtain 1-(2-amino-3-methylphenyl)ethan-1-one.

$^1$H NMR (400 MHz, $CDCl_3$) δ2.18 (s, 3H), 2.60 (s, 3H), 6.62 (t, J=7.6 Hz, 1H), 7.20-7.22 (m, 1H), 7.64 (dd, J=8.0, 0.8 Hz, 1H).

Example-3: Synthesis of 1-(2-amino-5-chloro-3-methylphenyl)-2,2,2-trichloroethan-1-one

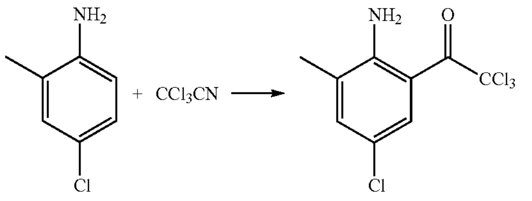

(1) (3)

A solution of anhydrous toluene (15 mL) and 4-chloro-2-methylaniline (0.840 mL, 7.06 mmol was cooled in an ice-bath under nitrogen atmosphere. To this stirred solution, a 1 M solution of boron trichloride in dichloromethane (7.77 mL, 7.77 mmol) was added drop wise over a period of 15 minutes under stirring. Further to this reaction mixture, trichloroacetonitrile (4.25 mL, 42.4 mmol) was added over a period of 15 minutes, followed by the addition of aluminium chloride (1.130 g, 8.47 mmol). The reaction mixture was stirred for further 10 minutes, and then it was heated gradually to 85° C. and maintained at this temperature for 20 h. The reaction mixture was cooled to room temperature, water (4 mL) was added and the reaction mixture was extracted with ethyl acetate (2×20 mL). The combined organic layers were washed with water and concentrated under reduced pressure to obtain a crude product. The crude product was purified by flash chromatography to obtain 1-(2-amino-5-chloro-3-methylphenyl)-2,2,2-trichloroethan-1-one.

$^1$H NMR (400 MHz, DMSO-$d_6$) δ2.17 (s, 3H), 7.36 (d, J=1.6 Hz, 1H), 7.43 (s, 2H), 7.96 (d, J=2.4 Hz, 1H).

$^{13}$C NMR (100 MHz, DMSO-$d_6$) δ17.67, 96.14, 106.51, 116.52, 127.83, 127.97, 135.7, 151.97, 180.2.

Example-4: Synthesis of 2-amino-5-chloro-N,3-dimethylbenzamide

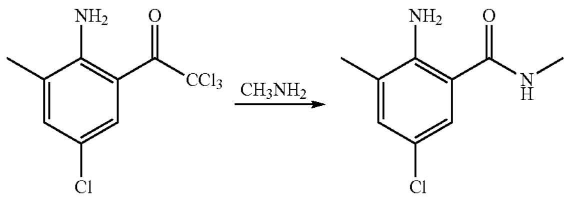

(3) (4)

To a mixture of n-hexane (5 mL) and 1-(2-amino-5-chloro-3-methylphenyl)-2,2,2-trichloroethan-1-one (280 mg, 0.976 mmol), a 2 M solution of methylamine (0.976 mL, 1.951 mmol) in tetrahydrofuran (5 mL) was added drop wise at room temperature under stirring. The reaction mixture was stirred further at 25° C. for 20 h. After completion of the reaction, the reaction mixture was concentrated under reduced pressure and diluted again with hexane (5 mL) during which a solid precipitated. The solid was collected by filtration and washed with n-hexane (20 mL) to obtain 2-amino-5-chloro-N,3-dimethylbenzamide (77% yield, 97.5% HPLC purity).

$^1$H NMR (400 MHz, $CDCl_3$) δ2.14 (s, 3H), 2.96 (d, J=4.8 Hz, 3H), 5.53 (s, 2H), 6.00 (s, 1H), 7.09-7.10 (m, 1H), 7.16 (d, J=1.8 Hz).

Example-5: Synthesis of 2-amino-5-chloro-N,3-dimethylbenzamide

Step-1

Synthesis of 1-(2-amino-3-methylphenyl)ethan-1-one

To an ice-cold solution of o-toluidine (20 g, 187 mmol) in toluene (200 mL), boron trichloride (224 mL, 224 mmol) was added drop wise at 0-5° C., and the reaction mixture was stirred at 0-5° C. for 0.5 h. Acetonitrile (58.5 mL, 1120 mmol) was added drop wise at 0-5° C. followed by the addition of aluminium chloride (29.9 g, 224 mmol). Stirring was continued at the same temperature for 30 minutes. The reaction temperature was raised slowly to 80° C. and maintained at the same level for 20 h. After completion of the reaction, the reaction mass was cooled to 0-5° C. and quenched by slow addition of water (200 mL). After quenching, the reaction mass was stirred further at 80° C. 1 h. After cooling to room temperature, the organic layer was separated and the aqueous layer was adjusted to pH 4-5. The aqueous layer was re-extracted with toluene (2×100 mL). The combined organic layers were washed with water (100 mL), dried over anhydrous sodium sulphate and concentrated under reduced pressure to obtain 1-(2-amino-3-methylphenyl)ethan-1-one (15 g; 54% yield).

$^1$H-NMR ($CDCl_3$, 400 MHz): δ7.65 (m, 1H), 7.21 (m, 1H), 6.60 (dd, J=8.2, 7.0 Hz, 1H), 6.59 (m, 2H), 2.59 (s, 3H), 2.19 (s, 3H);

$^{13}$C-NMR ($CDCl_3$, 100 MHz) δ201.3, 148.6, 135.0, 130.0, 123.3, 117.5, 115.0, 28.0, 17.1;

MS: m/z=150.05 [M+H]

Step-2a to 2c

Synthesis of 5-chloro-2-((ethoxycarbonyl)amino)-3-methylbenzoic acid from 1-(2-amino-3-methylphenyl)ethan-1-one Step 2a: To a stirred solution of 1-(2-amino-3-methylphenyl)ethan-1-one (1 g, 6.70 mmol) and potassium carbonate (1.853 g, 13.41 mmol) in acetone (10 mL), ethyl chloroformate (0.957 mL, 10.05 mmol) was added drop wise under nitrogen atmosphere at 25° C. The reaction mixture was continued to stir for 16 h at room temperature. After completion of the reaction, the reaction mixture was filtered through a pad of celite, and washed with acetone (2×15 mL). The filtrate was concentrated under reduced pressure to obtain a product which was used for the next step.

Step 2b: The product obtained in step 2a was taken in glacial acetic acid (12 mL) and heated to 90-95° C. Chlorine gas was purged thorough the reaction mixture. After completion of the reaction, the reaction mixture was cooled to room temperature. Nitrogen gas purged through the reaction mixture for 15 minutes to remove excess chlorine. Acetic acid was distilled off from the reaction mass to obtain a crude product which was used for the next step.

Step 2c: A solution of the product obtained in step 2b was taken up in tetrahydrofuran (THF) (20 mL) and was cooled to 0-5° C. To this solution, a solution of sodium hydroxide (1.755 g, 43.9 mmol) in water (18 mL) was added slowly and under stirring at room temperature for 1 h. Tetrahydrofuran (THF) was distilled off from the reaction mixture to obtain a residue. To this residue, ethyl acetate (50 mL) and water (25 mL) were added. The aqueous layer was separated and acidified to pH ~3-4 by addition of 6 N HCl, followed by extraction with ethyl acetate (2×50 mL). The combined organic layers were dried over anhydrous sodium sulphate and concentrated under reduced pressure to obtain 5-chloro-2-((ethoxycarbonyl)amino)-3-methylbenzoic acid (1.3 g, 51.3% yield).

$^1$H NMR (DMSO-$d_6$) δ9.8 (br s, 1H), 8.2 (br s, 1H), 7.81 (m, 1H), 7.41 (m, 1H), 4.21 (q, 2H), 2.30 (s, 3H), 1.26 (t, 3H), $^{13}$C-NMR (DMSO-$d_6$) δ170.3, 154.9, 137.8, 135.7, 130.9, 128.7, 128.9, 124.6, 62.16, 18.6, 14.3

MS: m/z=257.55 [M+H]

Step-3

Synthesis of 6-chloro-8-methyl-2H-benzo[d][1,3]oxazine-2,4(1H)-dione

To a stirred solution of 5-chloro-2-((ethoxycarbonyl)amino)-3-methylbenzoic acid (0.500 g, 1.940 mmol) in dioxane (10 mL), p-toluenesulfonic acid monohydrate (0.081 g, 0.427 mmol) was added and the reaction mixture was heated to reflux for 4 h. After completion of the reaction, the reaction mixture was concentrated to obtain a residue. To this residue, water (10 mL) was added under stirring. The solid which was finally obtained was filtered to afford 6-chloro-8-methyl-2H-benzo[d][1,3]oxazine-2,4(1H)-dione (0.21 g, 51% yield).

$^1$H-NMR ($CDCl_3$, 100 MHz) δ11.17 (s, 1H), 7.73 (dd, J=2.4 Hz & 0.5 Hz, 1H), 7.69 (dd, J=2.4 Hz & 0.7 Hz, 1H), 2.34 (s, 3H)

$^{13}$C-NMR ($CDCl_3$, 100 MHz) δ159.1, 146.9, 138.8, 137.1, 127.3, 126.7, 125.1, 111.9, 16.8

MS: m/z=210.05 [M−H]

Step-4: Synthesis of 1-(2-amino-5-chloro-3-methylphenyl)ethan-1-one

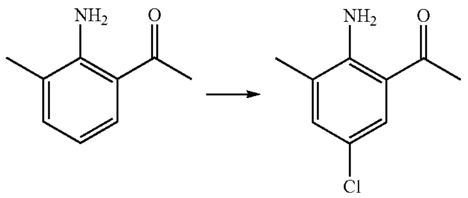

To a stirred solution of 1-(2-amino-3-methylphenyl)ethan-1-one (1 g, 6.70 mmol) in dichloroethane (DCE) (10 mL), hydrochloric acid (2.036 mL, 23.46 mmol) was added drop wise at 0° C., and stirring was continued at room temperature for 0.5 h. The reaction mixture was then cooled to 0° C. followed by drop wise addition of sodium hypochlorite (5.22 mL, 8.38 mmol) at 0° C. Stirring at room temperature was continued for 10 h. After completion of the reaction, the reaction mixture was extracted with dichloromethane (DCM) (2×25 mL). The combined organic layers were concentrated under reduced pressure to obtain a crude product which was triturated with methanol (10 mL) to obtain a solid which was filtered to afford 1-(2-amino-5-chloro-3-methylphenyl)ethan-1-one (0.6 g, 48.7% yield).

$^1$H-NMR ($CDCl_3$, 100 MHz) δ7.58 (d, 1H), 7.17 (d, 1H), 6.6 (br s, 2H), 2.57 (s, 3H), 2.16 (s, 3H).

$^{13}$C-NMR ($CDCl_3$, 100 MHz) δ200.15, 146.7, 134.8, 128.9, 125.8, 119.7, 118.4, 28.1, 17.1

MS: m/z=184.05 [M+H]

Step-5: Synthesis of 2-amino-5-chloro-N,3-dimethylbenzamide

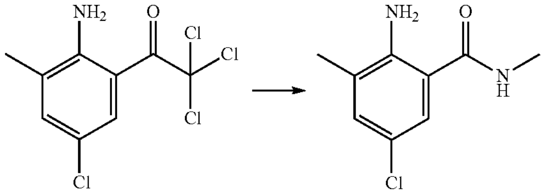

To a solution of 1-(2-amino-5-chloro-3-methylphenyl)-2,2,2-trichloroethan-1-one (0.250 g, 0.871 mmol) in hexane (2 mL), methylamine (2.178 mL, 4.36 mmol) was added slowly under stirring at room temperature. The solid obtained was filtered, washed with hexane (10 mL) to afford 2-amino-5-chloro-N,3-dimethylbenzamide (0.144 g, 83% yield).

$^1$H-NMR ($CDCl_3$, 100 MHz) δ: 7.16 (d, J=8.0 Hz, 1H), 7.09 (d, J=7.0 Hz, 1H), 6.06 (br s, 2H), 3.04 (d, 2H), 2.16 (s, 3H).

$^{13}$C-NMR ($CDCl_3$, 100 MHz) δ169.3, 145.4, 132.6, 125.6, 124.3, 120.3, 116.6, 26.6, 17.4

MS: m/z=199.05 [M+H]

Alternatively, 2-Amino-5-chloro-N,3-dimethylbenzamide can be prepared from 6-chloro-8-methyl-2H-benzo[d][1,3]oxazine-2,4(1H)-dione according to procedure described in prior art.

Example-6: Synthesis of 2-amino-5-bromo-N,3-dimethylbenzamide, Step-1: Synthesis of 1-(2-amino-3-methylphenyl)-2,2,2-trichloroethan-1-one To an ice-cold solution of o-toluidine (5.0 g, 46.7 mmol, 1 eq.) in toluene (10 mL), boron trichloride (56.0 mmol, 1.2 eq) was added drop-wise at 0-5° C., and stirring was continued at the same temperature for 0.5 h. To this solution, 2,2,2-trichloroacetonitrile (40.4 g, 6 eq) was added drop-wise at 0-5° C. followed by the addition of aluminium chloride (56.0 mmol, 1.2 eq). After stirring the reaction mixture at 0-5° C. for further 0.5 h, the reaction temperature was raised slowly to 80° C. and maintained at the same temperature for 20 h under stirring. The reaction mass was cooled to 0-5° C. and quenched by slow addition of water, followed by further to stirring at 80° C. for 1 h. The reaction mixture was cooled to 25° C. and the organic layer was separated. The aqueous layer was re-extracted with toluene (100 mL×2). The combined organic layers were concentrated under reduced pressure to obtain 1-(2-amino-3-methylphenyl)-2,2,2-trichloroethan-1-one (4.6 g, 35.6% yield).

$^1$H-NMR ($CDCl_3$, 100 MHz): δ8.21 (d, J=8.0 Hz, 1H), 7.26 (d, J=8.0 Hz, 1H), 6.59 (dd, 1H), 6.1 (br s, 2H), 2.2 (s, 3H).

$^{13}C$ NMR ($CDCl_3$, 100 MHz): δ182.1, 152.1, 136.3, 131.0, 124.0, 114.4, 108.2, 96.9, 17.6

MS: m/z=254.3 $[M+H]^+$

Step-2: Synthesis of 1-(2-amino-5-bromo-3-methylphenyl)-2,2,2-trichloroethan-1-one To an ice-cold solution of 1-(2-amino-3-methylphenyl)-2,2,2-trichloroethan-1-one (0.5 g, 1.98 mmol, 1 eq) in acetonitrile (5 mL), N-bromosuccinimide (0.352 g, 1.98 mmol, 1.0 eq) was added, and the reaction mixture was stirred at 0° C. for 1 h. After completion of the reaction, the reaction mass was quenched by addition of water and extracted with ethyl acetate (2×25 mL). The combined organic layers were washed with saturated sodium bicarbonate solution (2×25 mL). The organic phase was dried over anhydrous sodium sulphate and concentrated under reduced pressure to obtain 1-(2-amino-5-bromo-3-methylphenyl)-2,2,2-trichloroethan-1-one (0.55 g, 84% yield).

$^1H$ NMR (DMSO-$d_6$, 400 MHz): δ8.51 (d, 1H), 7.52 (d, 1H), 2.43 (s, 3H);

$^{13}C$ NMR (DMSO-$d_6$, 100 MHz): δ174.0, 145.9, 131.4, 130.3, 129.5, 128.4, 117.6, 94.6, 21.4; MS: m/z=332.75 $[M+H]^+$

Step-1a: Synthesis of 1-(2-amino-5-bromo-3-methylphenyl)-2,2,2-trichloroethan-1-one To an ice-cold solution of 4-bromo-2-methylaniline (10.0 g, 53.7 mmol, 1 eq.) in toluene (100 mL), boron trichloride (64.5 mmol, 1.2 eq) was added drop wise at 0-5° C., and the reaction mixture was stirred at 0-5° C. for 0.5 h. Then, 2,2,2-trichloroacetonitrile (46.6 g, 322 mmol, 6.0 eq) was added drop wise at 0-5° C. followed by the addition of aluminium chloride (64.5 mmol, 1.5 eq). After stirring the reaction mixture at 0-5° C. for 0.5 h, the reaction temperature was raised slowly to 80° C. and maintained at the same temperature for 20 h under stirring. The reaction mass was cooled to 0-5° C. and quenched by slow addition of water. The reaction mass was continued to stir at 80° C. for 1 h. After cooling the reaction mass to room temperature, the organic layer was separated. The aqueous layer was re-extracted with toluene (200 mL×2). The combined organic layers were concentrated under reduced pressure to obtain a crude material was taken for the next step. 1-(2-amino-5-bromo-3-methylphenyl)-2,2,2-trichloroethan-1-one $^1H$ NMR (DMSO-$d_6$, 400 MHz): δ8.51 (d, 1H), 7.52 (d, 1H), 2.43 (s, 3H);

$^{13}C$ NMR (DMSO-$d_6$, 100 MHz): δ174.0, 145.9, 131.4, 130.3, 129.5, 128.4, 117.6, 94.6, 21.4; MS: m/z=332.75 $[M+H]^+$

Step-3a: Synthesis of 2-amino-5-bromo-3-methylbenzoic acid

To a solution of 1-(2-amino-5-bromo-3-methylphenyl)-2,2,2-trichloroethan-1-one (0.5 g,) in tetrahydrofuran (THF) (2 mL), 6 M sodium hydroxide solution (6.06 eq, 2 mL) was added, and the reaction mixture was stirred at 25° C. for 3 h. After completion of the reaction, ethyl acetate (10 mL) was added, and the organic layer was separated and kept aside. The aqueous layer was acidified to pH 5-6 and extracted with ethyl acetate (2×25 mL). The combined organic layers were dried over anhydrous sodium sulphate and concentrated under reduced pressure to obtain 2-amino-5-bromo-3-methylbenzoic acid (0.30 g, 65.9% yield).

$^1H$ NMR (DMSO-$d_6$, 400 MHz): δ7.67 (d, 1H), 7.30 (d, 1H), 2.09 (s, 3H);

$^{13}C$ NMR (DMSO-$d_6$, 100 MHz): δ168.8, 149.0, 136.3, 130.6, 126.2, 110.8, 104.5, 17.2;

MS: m/z=230.20 [M−H]

Step-4: Synthesis of 2-amino-5-bromo-N,3-dimethylbenzamide

To a solution of 1-(2-amino-5-bromo-3-methylphenyl)-2,2,2-trichloroethan-1-one (0.10 g, 0.302 mmol) in tetrahydrofuran (THF) (1 mL), methylamine in tetrahydrofuran (THF) (2 M, 0.23 mL, 1.5 eq) was added, and the reaction mixture was stirred at room temperature for 2 h. After completion of the reaction, the reaction mass was concentrated under reduced pressure to obtain 2-amino-5-bromo-N,3-dimethylbenzamide (0.072 g, 98% yield).

$^1H$ NMR (DMSO-$d_6$, 400 MHz): δ8.32 (br d, 1H), 7.49 (d, 1H), 7.22 (d, 1H), 6.35 (br s, 2H), 2.70 (d, 3H), 2.08 (s, 3H);

$^{13}C$ NMR (DMSO-$d_6$, 100 MHz): δ168.4, 146.8, 134.2, 127.7, 125.9, 116.1, 105.0, 26.0, 17.2; MS: m/z=242.85 $[M+H]^+$

Step-1b: Synthesis of 1-(2-amino-5-bromo-3-methylphenyl)ethan-1-one

To an ice-cold solution of 4-bromo-2-methylaniline (5.0 g, 10.75 mmol, 1 eq.) in toluene (50 mL), boron trichloride (21.5 mmol, 2.0 eq) was added drop wise at 0-5° C., and the reaction mixture was stirred for 0.5 h. To this solution, acetonitrile (2.65 g, 5 eq.) was added drop wise at 0-5° C. followed by the addition of aluminium chloride (16.12 mmol, 1.5 eq.). Stirring was continued at the same temperature for further 0.5 h. The reaction temperature was slowly raised to 80° C. and maintained at the same temperature for 20 h. After completion of the reaction, the reaction mass was cooled to 0-5° C. and quenched by slow addition of water. After quenching, the reaction mass was continued to stir at 80° C. for 1 h. After cooling to 25° C., the organic layer was separated. The aqueous layer was re-extracted with toluene (100 mL×2). The combined organic layers were concentrated under reduced pressure to obtain 1-(2-amino-5-bromo-3-methylphenyl)ethan-1-one which was taken for the next step.

$^1H$ NMR ($CDCl_3$, 400 MHz): δ7.72 (d, 1H), 7.29 (d, 1H), 6.13 (br s, 2H), 2.56 (s, 3H), 2.15 (s, 3H);

$^{13}C$ NMR (DMSO-$d_6$, 100 MHz): δ200.0, 147.5, 137.4, 132.0, 125.9, 118.5, 106.3, 28.1, 17.01; MS: m/z=229.95 $[M+H]^+$

Step-1c: Synthesis of 1-(2-amino-5-bromo-3-methylphenyl)ethan-1-one

To an ice-cold solution of 1-(2-amino-3-methylphenyl) ethan-1-one (5.0 g, 33.5 mmol, 1 eq.) in acetonitrile (50 mL), N-bromosuccinimide (5.96 g, 1.0 eq.) was added, and the reaction mixture was stirred at 0° C. for 1 h. After completion of the reaction, the reaction mass was quenched with water and extracted with ethyl acetate (2×50 mL). The combined organic layers were washed with a saturated solution of sodium bicarbonate (2×50 mL), dried over anhydrous sodium sulphate and concentrated under reduced pressure to obtain 1-(2-amino-5-bromo-3-methylphenyl) ethan-1-one (2.2 g, 28.8% yield).

$^1H$ NMR (DMSO-$d_6$, 400 MHz): δ7.74 (d, 1H), 7.32 (d, 1H), 7.04 (br s, 2H), 2.51 (s, 3H), 2.09 (s, 3H);

$^{13}C$ NMR (DMSO-$d_6$, 100 MHz): δ199.8, 148.3, 136.6, 131.6, 123.3, 117.6, 104.3, 28.1, 17.1;

MS: m/z=229.85 $[M+H]^+$

Step-2b: Synthesis of ethyl (2-acetyl-4-bromo-6-methylphenyl)carbamate

To a stirred solution of 1-(2-amino-5-bromo-3-methylphenyl)ethan-1-one (1.0 g, 4.38 mmol) in dioxane (10 mL), sodium hydroxide (8.76 mmol, 2.0 eq) was added, and the reaction mixture was stirred for 15 min at room temperature. The reaction mixture was cooled to 10° C., followed by the addition of ethyl chloroformate (2.0 eq). The reaction mixture was warmed slowly to room temperature and stirring was continued further for 2 h. After completion of the reaction, the reaction mass was extracted with ethyl acetate (2×25 mL). The combined organic layers were dried over anhydrous sodium sulphate and concentrated under reduced pressure to obtain ethyl (2-acetyl-4-bromo-6-methylphenyl)carbamate (0.9 g, 64.6% yield).

$^{1}$H NMR (DMSO-$d_6$, 400 MHz): δ—9.0 (br s, 1H), 7.60 (m, 2H), 4.05 (q, 2H), 2.42 (s, 3H), 2.21 (s, 3H), 1.63 (t, 3H);

$^{13}$C NMR (DMSO-$d_6$, 100 MHz) δ199.3, 154.4, 138.5, 137.7, 135.11, 132.8, 128.0, 117.9, 60.5, 29.5, 17.5, 14.5

MS: m/z=301.85 [M+H]

Step-3b: Synthesis of 5-bromo-2-((ethoxycarbonyl)amino)-3-methylbenzoic acid

Procedure: To a solution of ethyl (2-acetyl-4-bromo-6-methylphenyl)carbamate (1.0 g, 3.33 mmol, 1 eq.) in acetic acid (8.0 ml), chlorine gas was purged at 90-95° C. After completion of the reaction, the reaction mass was distilled under reduced pressure to obtain ethyl (4-bromo-2-methyl-6-(2,2,2-trichloroacetyl)phenyl)carbamate which was then taken in tetrahydrofuran (THF) (8 mL) and cooled to 0° C. To this reaction mass, a solution of sodium hydroxide (0.66 g, 16.6 mmol, 5.0 eq) in water (8 ml) was added slowly and stirred at 25° C. for 1 h. After completion of the reaction, ethyl acetate (10 mL) was added to the reaction mixture. The organic layer was separated and kept aside. The aqueous layer was acidified to pH 5-6 and extracted with ethyl acetate (2×25 mL). The combined organic layers were dried over anhydrous sodium sulphate and concentrated under reduced pressure to obtain 5-bromo-2-((ethoxycarbonyl)amino)-3-methylbenzoic acid (0.87 g, 86% yield) as a brown solid.

$^{1}$H NMR (DMSO-$d_6$, 400 MHz): δ8.9 (br s, 1H), 7.62 (d. 1H), 7.54 (d, 1H), 4.1 (q, 2H), 2.30 (s, 3H), 1.19 (t, 3H);

$^{13}$C NMR (DMSO-$d_6$, 100 MHz) δ168.6, 166.8, 132.2, 135.7, 135.1, 130.1, 124.2, 117.5, 60.3, 21.0, 17.7;

MS: m/z=299.6 [M−H]

Step-4b: Synthesis of 6-bromo-8-methyl-2H-benzo[d][1,3]oxazine-2,4(1H)-dione

To a solution of 5-bromo-2-((ethoxycarbonyl)amino)-3-methylbenzoic acid in toluene (10 mL), p-TSA (0.14 g, 0.728 mmol, 0.22 eq) was added. The reaction mixture was refluxed for 3 h. After completion of the reaction, the reaction mass was diluted with ethyl acetate (20 mL). The organic layer was separated, washed with saturated solution of sodium bicarbonate solution, dried over anhydrous sodium sulphate and concentrated under reduced pressure to obtain a crude product. The crude product was purified by chromatography to obtain 6-bromo-8-methyl-2H-benzo[d][1,3]oxazine-2,4(1H)-dione (0.64 g, 76% yield) as a white solid.

$^{1}$H NMR (DMSO-$d_6$): δ11.16 (br s, 1H), 7.82 (d, J=1.6 Hz, 1H), 7.77 (d, J=1.6 Hz, 1H), 2.39 (s, 3H).

$^{13}$C-NMR (DMSO-$d_6$): δ158.9, 146.9, 139.7, 139.1, 128.6, 127.5, 114.3, 114.1, 112.3, 16.8

MS: m/z=255.6 [M−H]

2-Amino-5-bromo-N,3-dimethylbenzamide can be prepared from 6-bromo-8-methyl-2H-benzo[d][1,3]oxazine-2,4(1H)-dione according to procedure described in prior art.

Example-7: Synthesis of 2-amino-5-cyano-N,3-dimethylbenzamide

Step-a: Synthesis of 1-(2-amino-5-bromo-3-methylphenyl)ethan-1-one

To an ice-cold solution of 1-(2-amino-3-methylphenyl)ethan-1-one (5.0 g, 33.5 mmol, 1 eq) in acetonitrile (50 mL), N-bromosuccinimide (5.07 g, 28.5 mmol) was added, and the reaction mixture was stirred at 0° C. for 1 h. After completion of the reaction, the reaction mass was quenched by addition of water and extracted with ethyl acetate (2×50 mL). The combined organic layers were washed with saturated sodium bicarbonate solution (2×50 mL), dried over anhydrous sodium sulphate and concentrated under reduced pressure to obtain 1-(2-amino-5-bromo-3-methylphenyl)ethan-1-one (1.6 g, 21% yield).

$^{1}$H NMR (DMSO-$d_6$, 400 MHz): δ7.74 (d, 1H), 7.32 (d, 1H), 7.04 (br s, 2H), 2.51 (s, 3H), 2.09 (s, 3H);

$^{13}$C NMR (DMSO-$d_6$, 100 MHz): δ199.8, 148.3, 136.6, 131.6, 123.3, 117.6, 104.3, 28.1, 17.1;

MS: m/z=229.85 $[M+H]^+$

Step-b: Synthesis of 3-acetyl-4-amino-5-methylbenzonitrile

To a solution of 1-(2-amino-5-bromo-3-methylphenyl)ethan-1-one (2 g, 8.77 mmol) in N,N-dimethylformamide (DMF) (12 mL), potassium iodide (0.146 g, 0.877 mmol) and copper (I) cyanide (1.178 g, 13.15 mmol) were added under nitrogen atmosphere at 25-30° C. The reaction mass was heated to 150-152° C. and stirred for 13 h at the same temperature. After completion of the reaction, the reaction mass was poured into ice cold water (60 mL) followed by the addition of aqueous ammonia (3 mL), stirred for 20 minutes and filtered. The filtrate was acidified with diluted hydrochloric acid (1 N) to adjust a pH of about 4-5. The precipitated solid was filtered, washed with water (50 mL) and dried to obtain the product 3-acetyl-4-amino-5-methylbenzonitrile (0.5 g, 32.7% yield).

$^{1}$H NMR (400 MHz, $CDCl_3$): δ7.97 (d, 1H, J=1.6 Hz), 7.38 (d,1H, J=1.6 Hz), 2.60 (s,3H) 2.17 (s, 3H); IR (2214.32 $cm^{-1}$); MS: m/z=172.9 [M−1].

Step-c: Synthesis of 2-amino-5-bromo-3-methylbenzoic acid

A stirred solution of sodium hydroxide (10.72 g, 268 mmol) in water (50 mL) was cooled to 0° C. Bromine (8.03 g, 50.3 mmol) was added drop wise by maintaining the reaction temperature at 0-2° C., and stirring was continued further for 30 minutes below 5° C. A solution of 1-(2-amino-3-methylphenyl)ethan-1-one (5 g, 33.5 mmol) in 1,4-dioxane (20 mL) was added to the reaction mass at 0-2° C. The reaction temperature was brought to 50° C., and stirring was continued at the same temperature for 5 h. After completion of the reaction, the reaction mass was cooled to room temperature, acidified to pH 4-5 by addition of hydrochloric acid (2 N) and extracted with ethyl acetate (2×50 mL). The combined organic layers were concentrated under reduced pressure to obtain a crude product which was purified by flash column chromatography to obtain 2-amino-5-bromo-3-methylbenzoic acid (4.2 g, 55% yield).

$^1$H NMR (DMSO-$d_6$, 400 MHz): δ7.67 (d, 1H), 7.30 (d, 1H), 2.09 (s, 3H);

$^{13}$C NMR (DMSO-$d_6$, 100 MHz): δ168.8, 149.0, 136.3, 130.6, 126.2, 110.8, 104.5, 17.2;

MS: m/z=230.20 [M−H].

Example-8: Synthesis of 2-amino-5-cyano-3-methylbenzoic acid

To a stirred solution of 2-amino-5-bromo-3-methylbenzoic acid (2 g, 8.69 mmol) in N,N-dimethylformamide (DMF) (12 mL), potassium iodide (0.144 g, 0.869 mmol) and copper (I) cyanide (1.168 g, 13.04 mmol) were added under nitrogen atmosphere at 25-30° C. The reaction mass was heated to 150-152° C. and stirred for 13 h at the same temperature. After completion of the reaction, the reaction mass was poured into ice water (60 mL), followed by the addition of aqueous ammonia (3 mL), and stirring was continued for 20 minutes, followed by filtering. The filtrate was acidified by addition of dilute hydrochloric acid (1 N) to adjust a pH of about 4-5. The precipitated solid was filtered, washed with water (50 mL) and dried to obtain 2-amino-5-cyano-3-methylbenzoic acid (0.6 g, 39.2% yield).

$^1$H NMR (400 MHz, DMSO-$d_6$): δ13.01 (bs, 1H), 7.96 (d, 1H J=1.6 Hz), 7.50, (d, 1H, J=1.6 Hz), 7.35 (bs, 2H), 2.11 (s, 3H); FTIR (2223.96 $cm^{-3}$); MS: m/z=175 [M−1]

Example -9: Synthesis of 2-amino-5-cyano-N,3-dimethylbenzamide

Step-a: Synthesis of 4-amino-3-methyl-5-(2,2,2-trichloroacetyl)benzonitrile

To an ice-cold solution of 4-amino-3-methylbenzonitrile (5 g, 37.8 mmol) in toluene (50 mL), boron trichloride (91 mL, 91 mmol) was added drop wise at 0-5° C., and the reaction mixture was stirred for 0.5 h. To this reaction mixture, cyanotrichloromethane (32.8 g, 227 mmol) was added drop wise at 0-5° C. followed by the addition of aluminium chloride (6.05 g, 45.4 mmol). The reaction mixture was stirred at 0-5° C. for 0.5 h. The reaction temperature was raised to 80° C. and maintained at the same level for 20 h. After completion of the reaction, the reaction mass was cooled to 0-5° C. and quenched by the addition of water (50 mL). After quenching, the reaction mass was continued to stir at 80° C. for 1 h. After cooling the reaction mixture to room temperature, ethyl acetate (20 mL) was added to the reaction mass, which was then filtered. The organic layer was separated and the aqueous layer was re-extracted with ethyl acetate (20 mL). The combined organic layers were concentrated under reduced pressure to obtain 3.5 g crude of 4-amino-3-methyl-5-(2,2,2-trichloroacetyl) benzonitrile. The crude as such was taken for the next steps.

Step-b: Synthesis of 2-amino-5-cyano-N,3-dimethylbenzamide

To a stirred mixture of 4-amino-3-methyl-5-(2,2,2-trichloroacetyl) benzonitrile (500 mg, 1.8 mmol) and tetrahydrofuran (THF) (5 mL), methylamine (2 M in tetrahydrofuran (THF), 1.8 mL, 3.6 mmol) was added drop wise at room temperature under nitrogen atmosphere. The reaction mixture was stirred at 25° C. for 4 h. After completion of the reaction, the reaction mixture was concentrated and diluted with hexane (20 mL), during which a solid precipitated. The solid was collected by filtration and washed with n-hexane (10 mL) to obtain 2-amino-5-chloro-N,3-dimethylbenzamide (241 mg, 71% yield).

$^1$H NMR (400 MHz, $CDCl_3$) δ8.40 (d, J=3.6 Hz, 1H), 7.80 (d, J=1.2 Hz, 1H), 7.41 (s, 1H), 7.15 (br s, 2H), 2.08 (s, 3H); MS: m/z=188 [M−H]

Step-c: Synthesis of 2-amino-5-cyano-3-methylbenzoic acid

A stirred mixture of 4-amino-3-methyl-5-(2,2,2-trichloroacetyl) benzonitrile (1 g, 3.60 mmol) and tetrahydrofuran (THF) (8 mL) was cooled to 0-5° C. A solution of sodium hydroxide (1.22 g, 14.4 mmol) in water (12 mL) was added slowly, and stirring was continued for 2 h at room temperature. After completion of the reaction, tetrahydrofuran (THF) was distilled off from the reaction mixture followed by the addition of ethyl acetate (10 mL) and water (15 mL). The aqueous layer was separated and acidified by addition of 6 N hydrochloric acid to adjust a pH level of 3-4; after which it was extracted with of ethyl acetate (10 mL). The combined organic layers were concentrated under reduced pressure to obtain 2-amino-5-cyano-3-methylbenzoic acid (0.4 g, 63% yield).

$^1$H NMR (DMSO-$d_6$) δ12.5 (br s, 1H), 8.36 (s, 1H), 7.95 (d, J=2 Hz, 1H), 7.41 (bs, 2H), 1.89 (s, 3H); $^{13}$C-NMR (DMSO-$d_6$) δ171.6, 152.90, 135.56, 134.34, 124.61, 124.21, 119.72, 95.25, 21.75; MS: m/z=175 [M−H]

Step-d: Synthesis of 5-cyano-2-((ethoxycarbonyl)amino)-3-methylbenzoic acid

To a solution of 2-amino-5-cyano-3-methylbenzoic acid (0.5 g, 2.84 mmol) and potassium carbonate (0.98 g, 7.10 mmol) in acetone (5 mL), ethyl carbonochloridate (0.54 mL, 5.68 mmol)) was added drop wise under nitrogen atmosphere at 25° C. The reaction mixture was continued to stir for 16 h at room temperature. After completion of the reaction, the reaction mass was filtered through a pad of celite. The celite bed was washed with acetone (5 mL) and concentrated to obtain 5-cyano-2-((ethoxycarbonyl)amino)-3-methylbenzoic acid (0.16 g, 22% yield). The material was used in the next step without further purification.

Step-e: Synthesis of 8-methyl-2,4-dioxo-1,4-dihydro-2H-benzo[d][1,3]oxazine-6-carbonitrile To a stirred solution of 2-amino-5-cyano-3-methylbenzoic acid (0.5 g, 2.84 mmol) and triethylamine (TEA) (0.870 mL, 6.24 mmol) in dichloromethane (DCM) (5 mL), a solution of triphosgene (0.926 g, 3.12 mmol, 1.1 eq.) in dichloromethane (DCM) (3 mL) was added drop wise at 0° C. The reaction mixture was stirred at 25° C. for 3 h. After completion of the reaction, saturated solution of sodium bicarbonate (30 mL) was added to the reaction mixture and extracted with dichloromethane (DCM) (2×25 ml). The combined organic layers were washed with brine, dried over anhydrous sodium sulphate and concentrated under reduced pressure to afford 8-methyl-2,4-dioxo-1,4-dihydro-2H-benzo[d][1,3]oxazine-6-carbonitrile (0.23 g, 1.13 mmol, 40% yield)

$^{1}$H NMR (DMSO-d6) δ9.83 (br s, 1H), 8.195 (d, J=1.6 Hz, 1H), 7.98 (d, J=1.6 Hz, 1H), 2.25 (s, 3H);

$^{13}$C-NMR (DMSO-d6) δ166.52, 146.83, 139.94, 136.51, 131.36, 126.38, 118.14, 111.60, 105.40, 17.82;

MS: m/z=201.35 [M−H]

2-Amino-5-cyano-N,3-dimethylbenzamide can be prepared from 8-methyl-2,4-dioxo-1,4-dihydro-2H-benzo[d][1,3]oxazine-6-carbonitrile according to procedure described in prior art.

Example-10: Synthesis of (Z), wherein $R^{10}$ is $CX_3$

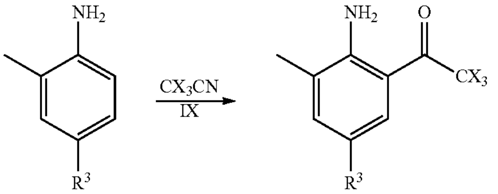

II

Z

Z-a: $R^3$ = Cl, X = Cl
Z-b: $R^3$ = H, X = Cl

To a stirred ice-cold solution of o-toluidine (20 g, 187 mmol) in toluene, boron trichloride (1.2 eq.) was added drop wise at 0-5° C. and stirring was continued at 0-5° C. for 0.5 h. Trihaloacetonitrile (5 eq.) was added drop wise at 0-5° C. followed by the addition of aluminium chloride (1.2 eq.), stirring was continued at the same temperature for 0.5 h. The reaction temperature was slowly raised to 80° C. and maintained at the same level for 20 h. The reaction mixture was cooled to 0-5° C. and quenched by slow addition of water. After quenching, stirring was continued at 80° C. for 1 h. The reaction mass was cooled to room temperature, and the organic layer was separated. The aqueous layer was adjusted to a pH level of 4-5 and re-extracted with toluene. The combined organic layers were concentrated under reduced pressure to obtain Z-a and Z-b.

Z-a

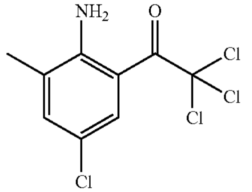

1-(2-amino-5-chloro-3-methylphenyl)-2,2,2-trichloroethan-1-one (Z-a)

$^{1}$H-NMR ($CDCl_3$, 100 MHz) δ: 7.97 (d, J=8.0 Hz, 1H), 7.43 (br s, 2H), 7.39 (d, J=7.0 Hz, 1H), 2.2 (s, 3H).

$^{13}$C-NMR ($CDCl_3$, 100 MHz) δ180.47, 151.9, 135.7, 128.0, 127.8, 116.5, 106.5, 96.1, 17.6

MS: m/z=286.5 [M+H]

Z-b

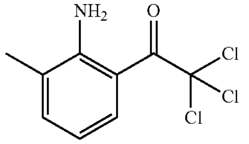

1-(2-amino-3-methylphenyl)-2,2,2-trichloroethan-1-one (Z-b)

$^{1}$H-NMR ($CDCl_3$, 100 MHz) δ: 8.21 (d, J=8.0 Hz, 1H), 7.26 (d, J=8.0 Hz, 1H), 6.59 (dd, 1H), 6.1 (br s, 2H), 2.2 (s, 3H).

$^{13}$C-NMR ($CDCl_3$, 100 MHz) δ182.1, 152.1, 136.3, 131.0, 124.0, 114.4, 108.2, 96.9, 17.6

MS: m/z=254.3 [M+H]

Having described the invention with reference to certain preferred embodiments, other embodiments will become apparent to one skilled in the art from consideration of the specification. It will be apparent to those skilled in the art that many modifications, both to materials and methods, may be practiced without departing from the scope of the invention.

The invention claimed is:

1. A process for the preparation of a compound of formula (Z) or a salt thereof:

Z

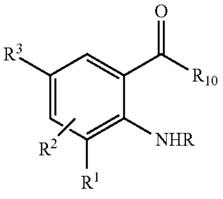

wherein, $R^1$ and $R^2$ are independently selected from the group consisting of hydrogen, halogen, $C_1$-$C_4$ alkyl, $C_1$-$C_4$ haloalkyl and $C_3$-$C_6$ cycloalkyl;

$R^3$ is selected from the group consisting of hydrogen, halogen, cyano, $C_1$-$C_4$ haloalkyl and $C_3$-$C_6$ cycloalkyl;

R is selected from the group consisting of hydrogen or $COR^{11}$;

wherein, $R^{11}$ is selected from the group consisting of $C_1$-$C_4$ alkoxy, O-benzyl and O-phenyl;

$R^{10}$ is selected from the group consisting of $CX_3$, $OR^9$, and $NR^{4a}R^{4b}$;

wherein, X represents halogen;

$R^9$ is selected from the group consisting of hydrogen and $C_1$-$C_4$ alkyl;

$R^{4a}$ and $R^{4b}$ are independently selected from the group consisting of hydrogen, $C_1$-$C_4$ alkyl, $C_3$-$C_6$ cycloalkyl, $C_3$-$C_6$ cycloalkyl-$C_1$-$C_4$ alkyl; and $NR^{4a}R^{4b}$ represent $—N═S(R^7R^8)═(O)_n$;

n represents an integer from 0-1;

$R^7$ and $R^8$ are independently selected from the group consisting of $C_1$-$C_4$ alkyl, $C_1$-$C_4$ haloalkyl, $C_3$-$C_6$ cycloalkyl and $C_3$-$C_6$ cycloalkyl-$C_1$-$C_4$ alkyl;

comprising step a) and one or more of steps b) to f):

a) reacting a substituted aniline of formula (II) with a trihaloacetonitrile of formula (IX) to obtain a compound of formula (Z), wherein $R^{10}$ is $CX_3$;

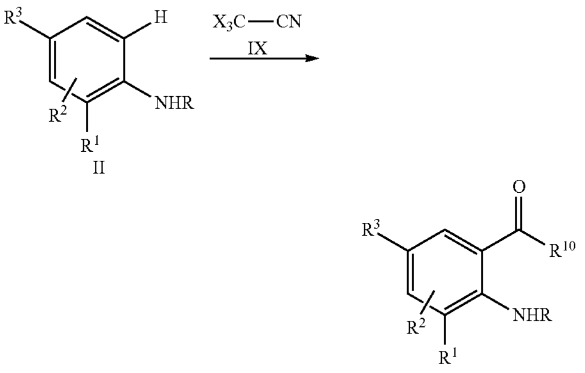

II

Z $R^{10}$ is $CX_3$ or i. reacting a substituted aniline of formula (II) with acetonitrile to obtain a substituted 2-aminoacetophenone of formula (III),

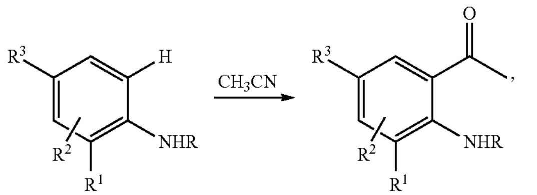

II

III and ii. halogenating the compound of formula (III) using a halogenating reagent to obtain a compound of formula (Z), wherein $R^{10}$ is $CX_3$;

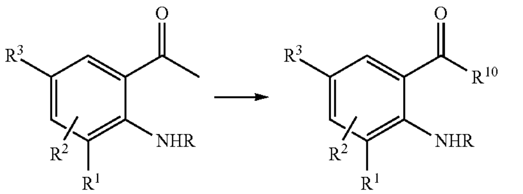

III

Z $R^{10}$ is $CX_3$ b) hydrolyzing the compound of formula (Z), wherein $R^{10}$ is $CX_3$, with a base or an acid to obtain a compound of formula (Z), wherein $R^{10}$ is $OR^9$ and $R^9$ is hydrogen;

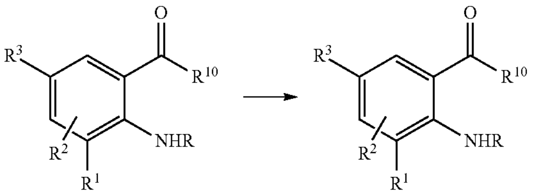

Z $R^{10}$ is $CX^3$

Z $R^{10}$ is $OR^9$ & $R^9$ is H or converting the compound of formula (III) to a compound of formula (Z), wherein $R^{10}$ is $OR^9$ and $R^9$ is hydrogen, without isolation of the compound of formula (Z) wherein $R^{10}$ is $CX_3$;

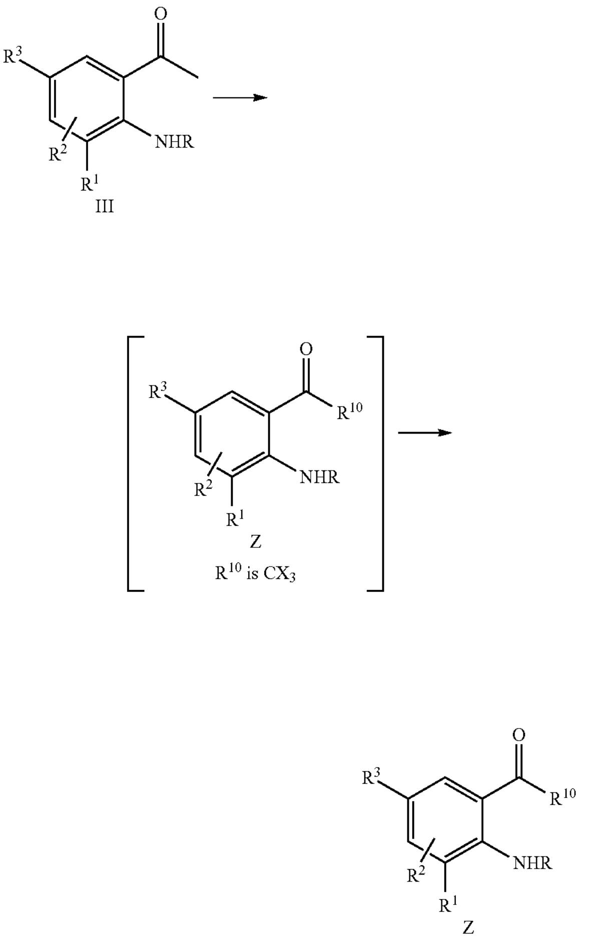

III

Z $R^{10}$ is $CX_3$

Z $R^{10}$ is $OR^9$ & $R^9$ is H c) converting the compound of formula (Z), wherein $R^{10}$ is $CX_3$, to a compound of formula (Z), wherein $R^{10}$ is $OR^9$ and $R^9$ is alkyl; with a base or an acid and in the presence of an alcoholic solvent;

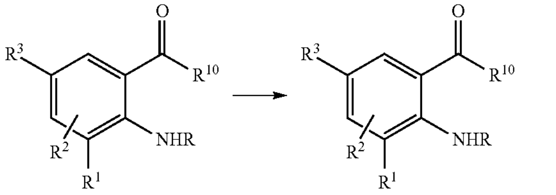

Z $R^{10}$ is $CX_3$

Z $R^{10}$ is $OR^9$ & $R^9$ is alkyl d) reacting the compound of formula (Z), wherein $R^{10}$ is $CX_3$, with a substituted amine of formula (VIII) to obtain a compound of formula (Z), wherein $R^{10}$ is $NR^{4a}R^{4b}$;

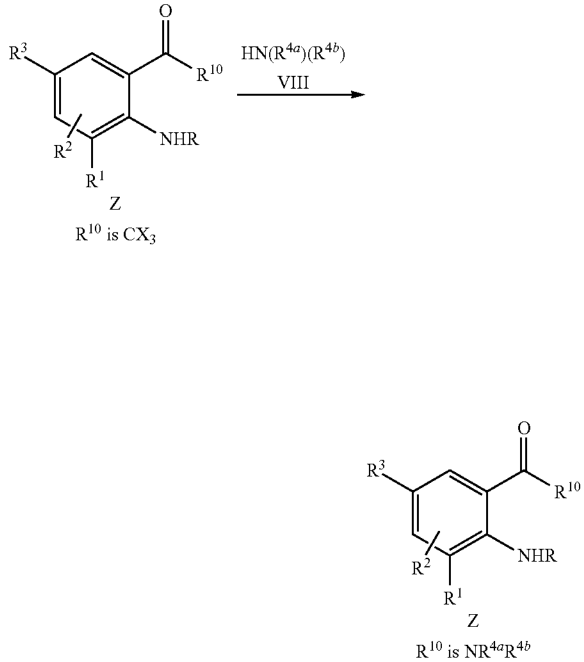

Z
$R^{10}$ is $CX_3$

Z
$R^{10}$ is $NR^{4a}R^{4b}$ e) reacting the compound of formula (Z), wherein $R^{10}$ is $OR^9$ and $R^9$ is hydrogen; with a substituted amine of formula (VIII) and a coupling reagent or a halogenating reagents and optionally in the presence of a base to obtain a compound of formula (Z), wherein $R^{10}$ is $NR^{4a}R^{4b}$;

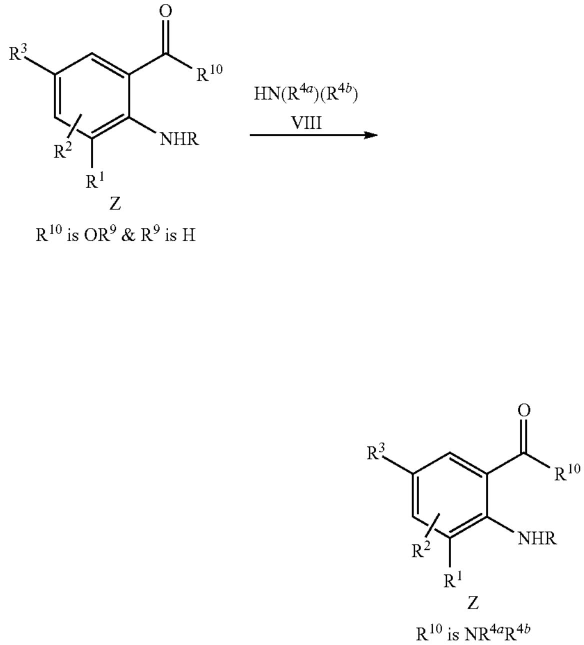

Z
$R^{10}$ is $OR^9$ & $R^9$ is H

Z
$R^{10}$ is $NR^{4a}R^{4b}$ or i. reacting the compound of formula (Z), wherein $R^{10}$ is $OR^9$ and $R^9$ is hydrogen; with an acid to obtain a compound of formula (IVa),

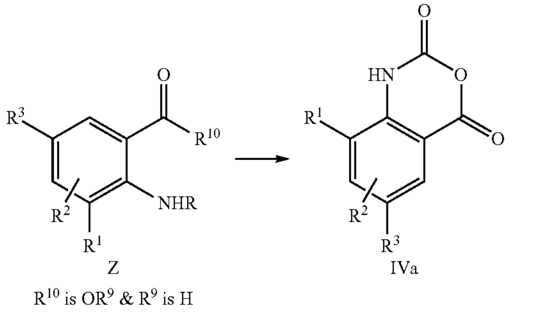

Z
$R^{10}$ is $OR^9$ & $R^9$ is H

IVa and ii. reacting the compound of formula (IVa) with a substituted amine of formula (VIII) to obtain compound of formula (Z), wherein $R^{10}$ is $NR^{4a}R^{4b}$;

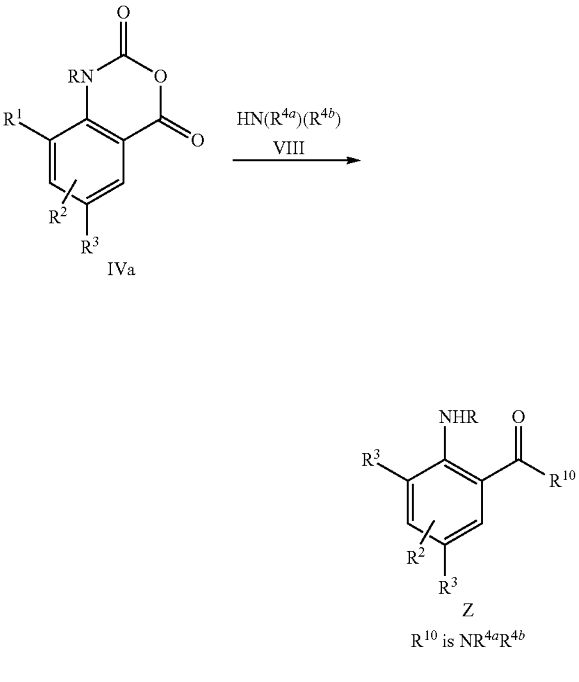

IVa

Z
$R^{10}$ is $NR^{4a}R^{4b}$ f) reacting the compound of formula (Z), wherein $R^{10}$ is $OR^9$ and $R^9$ is $C_1$-$C_4$ alkyl; with a substituted amine of formula (VIII) in the presence of a base to obtain a compound of formula (Z), wherein $R^{10}$ is $NR^{4a}R^{4b}$;

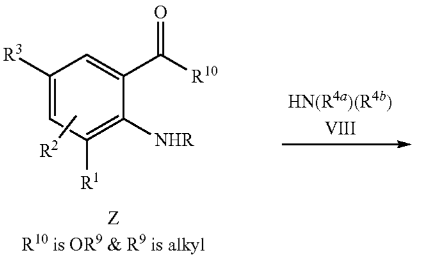

Z
$R^{10}$ is $OR^9$ & $R^9$ is alkyl

-continued

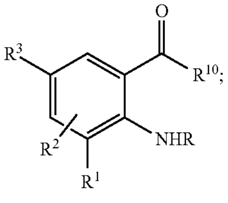

Z
$R^{10}$ is $NR^{4a}R^{4b}$ wherein R, $R^1$, $R^2$, $R^3$, $R^{4a}$ and $R^{4b}$ are as defined above.

2. The process according to claim 1, wherein said process further comprises the step of:

reacting the compound of formula (Z) wherein $R^{10}$ is $NR^{4a}R^{4b}$, with a compound of formula (VII), to obtain a compound of formula (I),

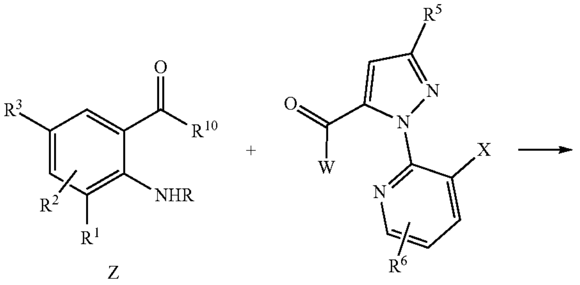

Z
$R^{10}$ is $NR^{4a}R^{4b}$

VII

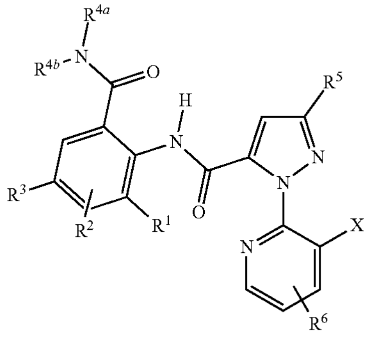

I wherein, W is OH, Cl, O—$C_1$-$C_4$ alkyl, O—C(O) $C_1$-$C_4$ alkyl or imidazolyl;

$R^5$ is selected from the group consisting of halogen, $C_1$-$C_4$ alkyl, $C_1$-$C_4$ haloalkyl, $CHF_2$, $CF_3$, $C_1$-$C_4$ alkoxy, $OCF_2H$, $OCH_2CF_3$, and -A-$C_3$-$C_5$ heterocyclyl;

wherein -A- is selected from the group consisting of direct bond, $CHR^6$, —O— or —S—; and said heterocyclyl may optionally be substituted with one or more group selected from hydrogen, halogen, cyano, $C_1$-$C_4$ alkyl and $C_1$-$C_4$ haloalkyl;

$R^6$ is selected from the group consisting of hydrogen, halogen, cyano, $C_1$-$C_4$ alkyl and $C_1$-$C_4$ haloalkyl;

X is halogen;

and R, $R^1$, $R^2$, $R^3$, $R^{4a}$ and $R^{4b}$ are as defined in claim 1 or i. reacting the compound of formula (Z) wherein $R^{10}$ represent $OR^9$ and $R^9$ is hydrogen with a compound of formula (VII), to obtain the compound of formula (IA),

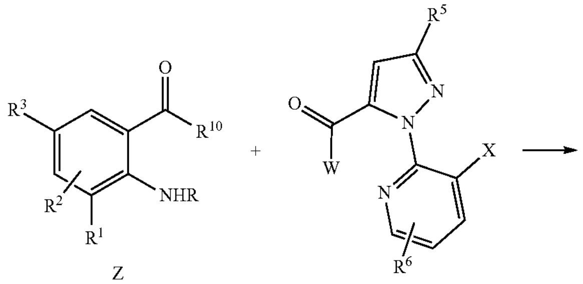

Z
$R^{10}$ is $OR^9$ & $R^9$ is H

VII

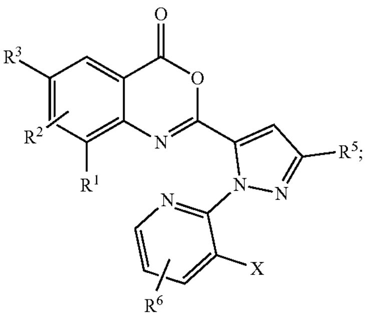

IA ii. reacting the compound of formula (IA) with a substituted amine of formula (VIII) to obtain compound of formula (I);

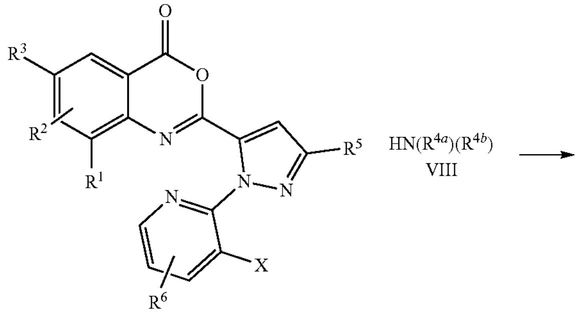

IA

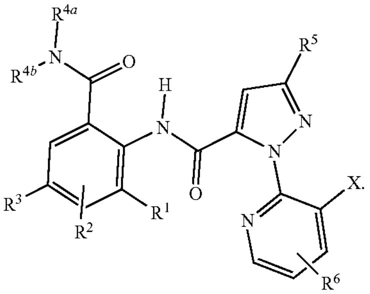

3. A process for the preparation of a compound of formula (Z) or a salt thereof,

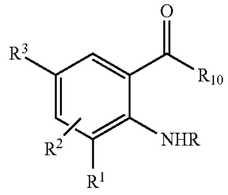

Z wherein, $R^1$ and $R^2$ are independently selected from the group consisting of hydrogen, halogen, $C_1$-$C_4$ alkyl, $C_1$-$C_4$ haloalkyl and $C_3$-$C_6$ cycloalkyl;

$R^3$ is selected from the group consisting of hydrogen, halogen, cyano, $C_1$-$C_4$ haloalkyl and $C_3$-$C_6$ cycloalkyl;

R is selected from the group consisting of hydrogen or $COR^{11}$;

wherein, $R^{11}$ is selected from the group consisting of $C_1$-$C_4$ alkoxy, O-benzyl and O-phenyl;

$R^{10}$ is selected from the group consisting of $CX_3$, $OR^9$, and $NR^{4a}R^{4b}$;

wherein, X represents halogen;

$R^9$ is selected from the group consisting of hydrogen and $C_1$-$C_4$ alkyl;

$R^{4a}$ and $R^{4b}$ are independently selected from the group consisting of hydrogen, $C_1$-$C_4$ alkyl, $C_3$-$C_6$ cycloalkyl, $C_3$-$C_6$ cycloalkyl-$C_1$-$C_4$ alkyl; and $NR^{4a}R^{4b}$ represent $-N{=}S(R^7R^8){=}(O)_n$;

n represents an integer from 0-1;

$R^7$ and $R^8$ are independently selected from the group consisting of $C_1$-$C_4$ alkyl, $C_1$-$C_4$ haloalkyl, $C_3$-$C_6$ cycloalkyl and $C_3$-$C_6$ cycloalkyl-$C_1$-$C_4$ alkyl;

comprising:

a) reacting a substituted aniline of formula (II) with a trihaloacetonitrile of formula (IX) to obtain a compound of formula (Z), wherein $R^{10}$ is $CX_3$;

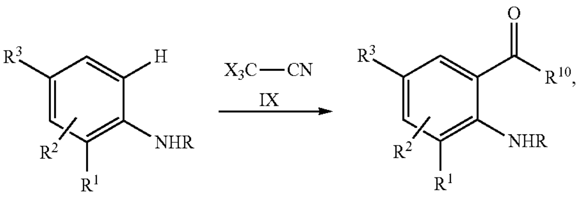

II

Z $R^{10}$ is $CX_3$ or i. reacting a substituted aniline of formula (II) with acetonitrile to obtain a substituted 2-aminoacetophenone compound of formula (III),

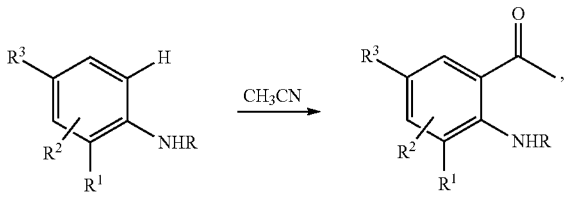

II

III and ii. halogenating the compound of formula (III) using a halogenating reagent to obtain a compound of formula (Z), wherein $R^{10}$ is $CX_3$;

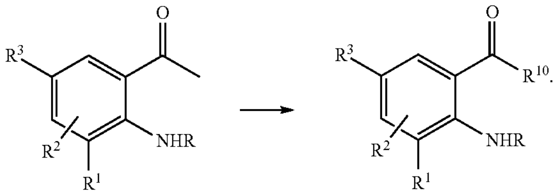

III

Z $R^{10}$ is $CX_3$

4. The process according to claim 1, wherein, said process for the synthesis of a compound of formula (Z), wherein $R^{10}$ is $OR^9$ and $R^9$ is hydrogen; comprises steps of:

b) hydrolyzing the compound of formula (Z), wherein $R^{10}$ is $CX_3$, with a base or an acid to obtain a compound of formula (Z), wherein $R^{10}$ is $OR^9$ and $R^9$ is hydrogen;

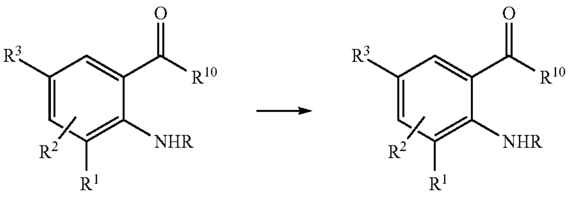

Z $R^{10}$ is $CX_3$

Z $R^{10}$ is $OR^9$ & $R^9$ is H or converting the compound of formula (III) to a compound of formula (Z), wherein $R^{10}$ is $OR^9$, and $R^9$ is hydrogen, without isolation of the compound of formula (Z) wherein $R^{10}$ is $CX_3$;

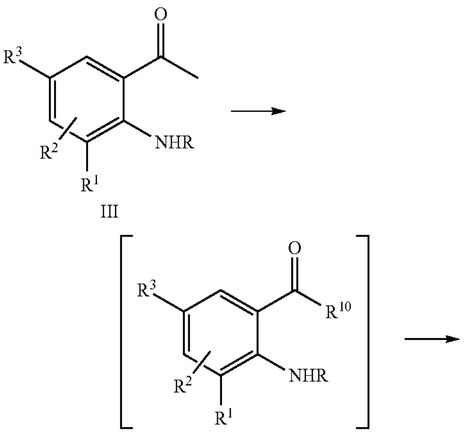

III

Z $R^{10}$ is $CX_3$

-continued

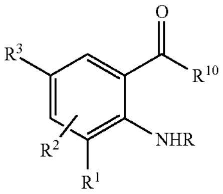

Z
$R^{10}$ is $OR^9$ & $R^9$ is H

5. The process according to claim 1, wherein, said process for the synthesis of a compound of formula (Z), wherein $R^{10}$ is $NR^{4a}R^{4b}$; comprises steps of d) reacting the compound of formula (Z), wherein $R^{10}$ is $CX_3$, with a substituted amine of formula (VIII) to obtain a compound of formula (Z), wherein $R^{10}$ is $NR^{4a}R^{4b}$;

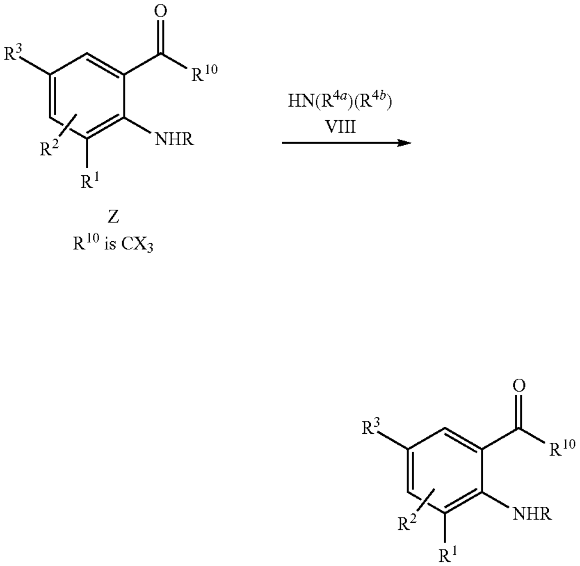

Z
$R^{10}$ is $CX_3$

Z
$R^{10}$ is $NR^{4a}R^{4b}$ e) reacting the compound of formula (Z), wherein $R^{10}$ is $OR^9$ and $R^9$ is hydrogen; with a substituted amine of formula (VIII) with coupling reagent or a halogenating reagents and optionally in the presence of a base to obtain a compound of formula (Z), wherein $R^{10}$ is $NR^{4a}R^{4b}$;

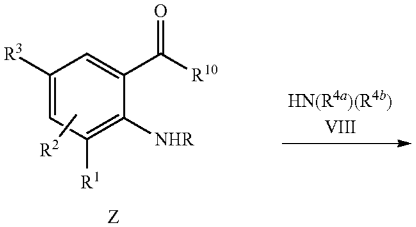

Z
$R^{10}$ is $OR^9$ & $R^9$ is H

-continued

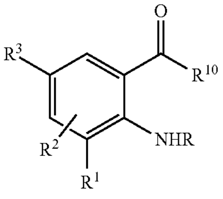

Z
$R^{10}$ is $NR^{4a}R^{4b}$ or i. reacting the compound of formula (Z), wherein $R^{10}$ is $OR^9$ and $R^9$ is hydrogen; with an acid to obtain a compound of formula (IVa),

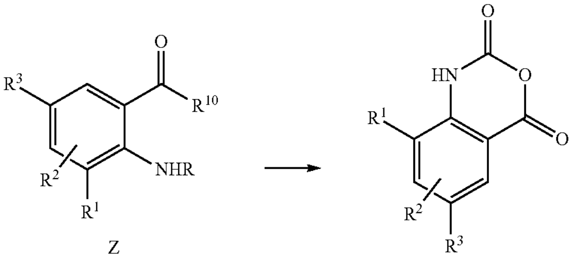

Z
$R^{10}$ is $OR^9$ & $R^9$ is H

IVa and ii. reacting the compound of formula (IVa) with a substituted amine of formula (VIII) to obtain compound of formula (Z), wherein $R^{10}$ is $NR^{4a}R^{4b}$;

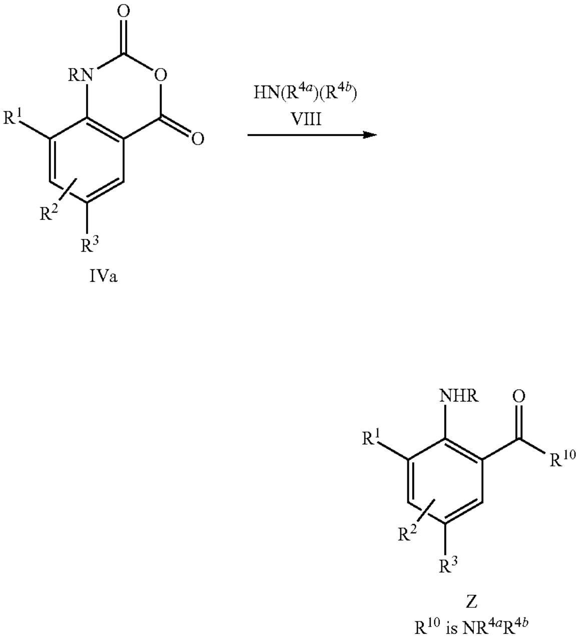

IVa

Z
$R^{10}$ is $NR^{4a}R^{4b}$ f) reacting the compound of formula (Z), where in $R^{10}$ is $OR^9$ and $R^9$ is $C_1$-$C_4$alkyl; with a substituted amine of formula (VIII) in the presence of a base to obtain a compound of formula (Z), wherein $R^{10}$ is $NR^{4a}R^{4b}$;

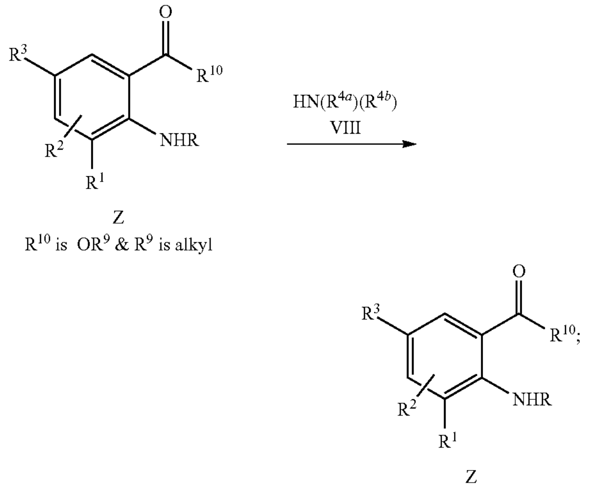

Z
$R^{10}$ is $OR^9$ & $R^9$ is alkyl

Z
$R^{10}$ is $NR^{4a}R^{4b}$ wherein R, $R^1$, $R^2$, $R^3$ $R^{4a}$, $R^{4b}$ and X are as defined above.

6. The process according to claim 1, wherein, said process for the synthesis of a compound of (Z), wherein $R^{10}$ is $CX_3$, and $R^3$ is halogen, from compound of formula (III), wherein $R^3$ is hydrogen, and all other variables are defined as in claim 1;

comprising, halogenating the compound of formula (III), wherein $R^3$ is hydrogen, using a halogenating reagent to obtain a compound of formula (Z), wherein $R^{10}$ is $CX_3$ and $R^3$ is halogen;

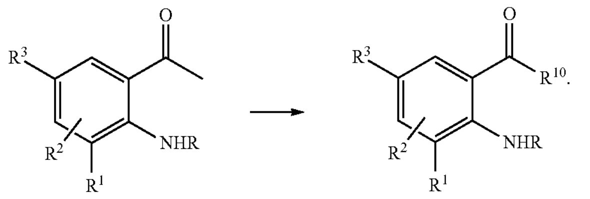
III
$R^3$ is H

Z
$R^{10}$ is $CX_3$ and $R^3$ is X

7. The process according to claim 2, wherein said compound of formula (I) is chlorantraniliprole, cyantraniliprole, cyclaniliprole, tetraniliprole, tetra-chlorantraniliprole, bromantraniliprole, dichlorantraniliprole or fluchlordiniliprole.

8. The process according to claim 1, wherein,
$R^1$ is methyl or halogen;
$R^2$ is hydrogen or halogen;
$R^3$ is halogen or cyano;
$R^{10}$ is $CX_3$, $OR^9$ or $NR^{4a}R^{4b}$;
$R^9$ is hydrogen, methyl, ethyl n-propyl, iso-propyl, iso-butyl, or tert-butyl,
$R^{4a}$ is methyl, ethyl, n-propyl, iso-propyl, cyclopropyl methylcyclopropyl, ethylcyclopropyl, iso-butyl, tert-butyl;
$R^{4b}$ is hydrogen or methyl,
X is halogen.

9. The process according to claim 1, wherein,
$R^1$ is methyl, chloro or bromo;
$R^2$ is hydrogen or fluoro;
$R^3$ is chloro, bromo or cyano;
X is halogen.

10. The process according to claim 2, wherein,
$R^1$ is methyl or halogen;
$R^2$ is hydrogen or halogen;
$R^3$ is halogen or cyano;
$R^{10}$ is $OR^9$ or $NR^{4a}R^{4b}$;
$R^9$ hydrogen, methyl, ethyl n-propyl, iso-propyl, iso-butyl, tert-butyl,
$R^{4a}$ is methyl, ethyl, n-propyl, iso-propyl, cyclopropyl methylcyclopropyl, ethylcyclopropyl, iso-butyl or tert-butyl;
$R^{4b}$ is hydrogen or methyl,
$R^5$ is selected from the group consisting of bromo, chloro, and -A-$C_3$-$C_5$ heterocyclyl;
wherein -A- is selected from the group consisting of direct bond, $CHR^6$, —O— and —S—; and said heterocyclyl may optionally be substituted with one or more group selected from hydrogen, halogen, cyano, $C_1$-$C_4$ alkyl and $C_1$-$C_4$ haloalkyl;
$R^6$ is selected from the group consisting of hydrogen, halogen, cyano, $C_1$-$C_4$ alkyl and $C_1$-$C_4$ haloalkyl.

11. The process according to claim 2, wherein, $R^1$ is methyl, chloro or bromo;
$R^2$ is hydrogen or fluoro;
$R^3$ is chloro, bromo or cyano;
$R^5$ is selected from the group consisting of bromo, chloro, and

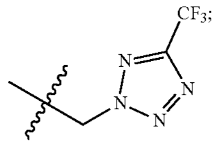 [SMILES: *Cn1nnc(C(F)(F)F)n1]

$R^6$ is selected from the group consisting of hydrogen, bromo, chloro, and fluoro.

12. The process according to claim 1, wherein said suitable acid is selected from hydrochloric acid, hydrobromic acid, sulfuric acid, formic acid, acetic acid, trifluoroacetic acid, propionic acid, methanesulfonic acid, benzenesulfonic acid, an acidic ion-exchange resin and a mixture thereof.

13. The process according to claim 1, wherein said suitable base is selected from ammonia, alkali or alkaline earth metal hydroxide or carbonate or bicarbonate, methylamine, dimethyl amine, diethyl amine, triethylamine, diisopropylamine, diisopropyl ethyl amine, pyridine, alkylated and dialkylated pyridines, dimethylamino pyridine, piperidine and mixtures thereof.

14. The process according to claim 1, wherein said suitable halogenating reagent is selected from HX, $SOCl_2$, $SO_2Cl_2$, $COCl_2$, $X_2$, $C(=O)(OCl_3)_2$, t-BuOCl, NaOCl, NaOBr, chloramine-T, N-halosuccinamides, methanesulfonyl chloride, $POX_3$, $PX_3$, $PX_5$ and metal halides; wherein X is Cl, Br, I or F.

15. The process according to claim 11, wherein said suitable halogenating reagent is selected from HX, $SOCl_2$, $X_2$, NaOCl, NaOBr and N-halosuccinamides.

16. The process as claimed in claim 1, wherein said reaction steps are carried out using suitable solvent selected from hexane, heptane, cyclohexane, methylcyclohexane, toluene, xylene, decalin, chlorobenzene, dichlorobenzene, dichloromethane, chloroform, tetrachloromethane, dichloroethane, trichloroethane, diethylether, diisopropyl ether, methyl tert-butyl ether, methyl tert-amyl ether, dioxane, tetrahydrofuran, 1,2-dimethoxy ethane, 1,2-diethoxyethane, anisole, acetonitrile, propionitrile, n- or iso-butyronitrile, benzonitrile, N,N-dimethylformamide, N,N-dimethylacetamide, N-methylformanilide, N-methylpyrrolidone, hexamethylphosphoric triamide, dimethyl sulfoxide, sulfones, sulfolane, methanol, ethanol, isopropanol, water and mixtures thereof.

17. A compound of formula (Z) or a salt thereof,

Formula (Z)

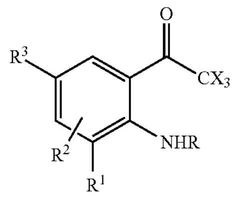

wherein, $R^1$ and $R^2$ are independently selected from the group consisting of hydrogen, halogen, $C_1$-$C_4$ alkyl, $C_1$-$C_4$ haloalkyl and $C_3$-$C_6$ cycloalkyl;

$R^3$ is selected from the group consisting of hydrogen, halogen, cyano, $C_1$-$C_4$ haloalkyl and $C_3$-$C_6$ cycloalkyl;

R is selected from the group consisting of hydrogen and $COR^{11}$;

wherein, $R^{11}$ is selected from the group consisting of $C_1$-$C_4$ alkoxy, O-benzyl and O-phenyl;

X represent chloro or bromo;

with the proviso that the compounds 1-(2-amino-5-chlorophenyl)-2,2,2-trichloroethan-1-one and 1-(2-amino-5-fluorophenyl)-2,2,2-trichloroethan-1-one, are excluded from the compounds of formula (Z).

* * * * *